United States Patent
Zhou et al.

(10) Patent No.: US 10,087,217 B2
(45) Date of Patent: Oct. 2, 2018

(54) ADENO-ASSOCIATED VIRUS WITH SITE-DIRECTED MUTAGENESIS AND SITE-DIRECTED MODIFICATION AND PREPARATION METHOD AND APPLICATION THEREOF

(71) Applicant: Peking University, Beijing (CN)

(72) Inventors: Demin Zhou, Beijing (CN); Chuanling Zhang, Beijing (CN); Sulong Xiao, Beijing (CN); Tianzhuo Yao, Beijing (CN); Yongxiang Zheng, Beijing (CN); Fei Yu, Beijing (CN); Longlong Si, Beijing (CN); Lihe Zhang, Beijing (CN)

(73) Assignee: Peking University, Beijing (CN)

( * ) Notice: Subject to any disclaimer, the term of this patent is extended or adjusted under 35 U.S.C. 154(b) by 5 days.

(21) Appl. No.: 15/033,723

(22) PCT Filed: Oct. 30, 2014

(86) PCT No.: PCT/CN2014/089880
§ 371 (c)(1),
(2) Date: May 2, 2016

(87) PCT Pub. No.: WO2015/062516
PCT Pub. Date: May 7, 2015

(65) Prior Publication Data
US 2016/0297855 A1  Oct. 13, 2016

(30) Foreign Application Priority Data

Oct. 30, 2013 (CN) .......................... 2013 1 0524527

(51) Int. Cl.
| | | |
|---|---|---|
| C12N 15/86 | (2006.01) | |
| C12N 7/00 | (2006.01) | |
| C07K 14/005 | (2006.01) | |
| A61K 48/00 | (2006.01) | |
| A61K 39/00 | (2006.01) | |
| A61K 39/23 | (2006.01) | |

(52) U.S. Cl.
CPC ............ *C07K 14/005* (2013.01); *A61K 39/23* (2013.01); *C12N 7/00* (2013.01); *C12N 15/86* (2013.01); *A61K 2039/53* (2013.01); *C12N 2750/14121* (2013.01); *C12N 2750/14122* (2013.01); *C12N 2750/14134* (2013.01); *C12N 2750/14143* (2013.01); *C12N 2750/14145* (2013.01); *C12N 2750/14151* (2013.01)

(58) Field of Classification Search
CPC ...... C12N 7/00; C12N 15/86; A61K 2039/53; A61K 39/23; C07K 14/005
See application file for complete search history.

(56) References Cited

FOREIGN PATENT DOCUMENTS

| | | | |
|---|---|---|---|
| CN | 102838663 | * | 12/2012 |
| CN | 102838663 A | | 12/2012 |
| WO | 2004/027019 A2 | | 4/2004 |
| WO | WO2004027019 | * | 4/2004 |
| WO | 2005/003294 A2 | | 1/2005 |
| WO | WO2005003294 | * | 1/2005 |
| WO | 2009/108274 A2 | | 9/2009 |
| WO | WO2009108274 | * | 9/2009 |
| WO | 2012/149160 A2 | | 11/2012 |

OTHER PUBLICATIONS

Rubino et al., "Chemoselective Modification of Viral Surfaces via Bioorthogonal Click Chemistry", Journal of Visualized Experiments, 2012, vol. 66, pp. 1-7.
Steinmetz et al., "Potato virus X as a novel platform for potential biomedical applications", Nano Letter, 2010, vol. 10, No. 1, pp. 305-312.
Wang et al., "Expanding the Genetic Code", Angewandte Chemie International Edition, 2004, vol. 44, No. 1, pp. 34-66.
European Extended Search Report, Application No. EP14857377.7 dated May 15, 2017.

* cited by examiner

*Primary Examiner* — Barry A Chestnut
(74) *Attorney, Agent, or Firm* — MacMillan, Sobanski & Todd, LLC

(57) ABSTRACT

The present invention relates to an adeno-associated virus with site-directed mutagenesis and site-specific modification, and a preparation method and uses thereof. Specifically, the present invention uses genetic code expansion techniques to incorporate non-natural amino acid into an adeno-associated virus capsid protein VP1 or fragment thereof, thereby obtaining an adeno-associated virus with site-directed mutagenesis using the non-natural amino acid. The adeno-associated virus with site-directed mutagenesis is equivalent to a wild-type virus in terms of production, transduction and mobility, can couple with other functional molecules, such as targeting molecules, and can carry a functional gene in a normal manner, which indicates that the adeno-associated virus with site-directed mutagenesis can be used as a tool adeno-associated virus, and applied in various aspects associated with adeno-associated virus such as finding adeno-associated virus binding proteins or using as target genetic therapy vector.

24 Claims, 13 Drawing Sheets
Specification includes a Sequence Listing.

SEQUENCE LISTING

<160> NUMBER OF SEQ ID NOS: 32

<210> SEQ ID NO 1
<211> LENGTH: 735
<212> TYPE: PRT
<213> ORGANISM: AAV2

<400> SEQUENCE: 1

```
Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255
```

-continued

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Gln
    450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
    530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys

|  | 675 | 680 | 685 |  |
|---|---|---|---|---|

Glu Asn Ser Lys Arg Trp Asn Pro Glu Ile Gln Tyr Thr Ser Asn Tyr
     690                    695                    700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
             725                  730                735

<210> SEQ ID NO 2
<211> LENGTH: 2208
<212> TYPE: DNA
<213> ORGANISM: AAV2

<400> SEQUENCE: 2

```
atggctgccg atggttatct tccagattgg ctcgaggaca ctctctctga aggaataaga      60
cagtggtgga agctcaaacc tggcccacca ccaccaaagc ccgcagagcg cataaggac     120
gacagcaggg gtcttgtgct tcctgggtac aagtacctcg acccttcaa cggactcgac     180
aagggagagc cggtcaacga ggcagacgcc gcggccctcg agcacgacaa agcctacgac     240
cggcagctcg acagcggaga caacccgtac ctcaagtaca accacgccga cgcggagttt     300
caggagcgcc ttaaagaaga tacgtctttt gggggcaacc tcggacgagc agtcttccag     360
gcgaaaaaga gggttcttga acctctgggc ctggttgagg aacctgttaa gacggctccg     420
ggaaaaaaga ggccggtaga gcactctcct gtggagccag actcctcctc gggaaccgga     480
aaggcgggcc agcagcctgc aagaaaaaga ttgaattttg gtcagactgg agacgcagac     540
tcagtacctg accccagcc tctcggacag ccaccagcag ccccctctgg tctgggaact     600
aatacgatgg ctacaggcag tggcgcacca atggcagaca taacgagggg cgccgacgga     660
gtgggtaatt cctcgggaaa ttggcattgc gattccacat ggatgggcga cagagtcatc     720
accaccagca cccgaacctg gcccctgccc acctacaaca accacctcta caaacaaatt     780
tccagccaat caggagcctc gaacgacaat cactactttg gctacagcac cccttggggg     840
tattttgact tcaacagatt ccactgccac ttttcaccac gtgactggca agactcatc     900
aacaacaact ggggattccg acccaagaga ctcaacttca agctctttaa cattcaagtc     960
aaagaggtca cgcagaatga cggtacgacg acgattgcca ataacctta cagcacggtt    1020
caggtgttta ctgactcgga gtaccagctc ccgtacgtcc tcggctcggc gcatcaagga    1080
tgcctcccgc cgttcccagc agacgtcttc atggtgccac agtatggata cctcaccctg    1140
aacaacggga gtcaggcagt aggacgctct tcattttact gcctggagta ctttccttct    1200
cagatgctgc gtaccggaaa caactttacc ttcagctaca cttttgagga cgttcctttc    1260
cacagcagct acgctcacag ccagagtctg gaccgtctca tgaatcctct catcgaccag    1320
tacctgtatt acttgagcag aacaaacact ccaagtggaa ccaccacgca gtcaaggctt    1380
cagtttctc aggccggagc gagtgacatt cgggaccagt ctaggaactg gcttcctgga    1440
ccctgttacc gccagcagcg agtatcaaag acatctgcgg ataacaacaa cagtgaatac    1500
tcgtggactg gagctaccaa gtaccacctc aatggcagag actctctggt gaatccgggc    1560
ccggccatgg caagccacaa ggacgatgaa gaaaagtttt tccctcagag cggggttctc    1620
atctttggga agcaaggctc agagaaaaca aatgtggaca ttgaaaaggt catgattaca    1680
gacgaagagg aaatcaggac aaccaatccc gtggctacgg agcagtatgg ttctgtatct    1740
accaacctcc agagaggcaa cagacaagca gctaccgcag atgtcaacac acaaggcgtt    1800
```

|  |  |  |  |  |  |
|---|---|---|---|---|---|
| cttccaggca | tggtctggca | ggacagagat | gtgtaccttc | aggggcccat | ctgggcaaag | 1860 |
| attccacaca | cggacggaca | ttttcacccc | tctcccctca | tgggtggatt | cggacttaaa | 1920 |
| caccctcctc | cacagattct | catcaagaac | accccggtac | ctgcgaatcc | ttcgaccacc | 1980 |
| ttcagtgcgg | caaagtttgc | ttccttcatc | acacagtact | ccacgggaca | ggtcagcgtg | 2040 |
| gagatcgagt | gggagctgca | gaaggaaaac | agcaaacgct | ggaatcccga | aattcagtac | 2100 |
| acttccaact | acaacaagtc | tgttaatgtg | gactttactg | tggacactaa | tggcgtgtat | 2160 |
| tcagagcctc | gccccattgg | caccagatac | ctgactcgta | atctgtaa |  | 2208 |

<210> SEQ ID NO 3
<211> LENGTH: 41
<212> TYPE: DNA
<213> ORGANISM: Artificial Sequence
<220> FEATURE:
<223> OTHER INFORMATION: Synthetic

<400> SEQUENCE: 3
ctcatcgacc agtacctgta ttagttgagc agaacaaaca c            41

<210> SEQ ID NO 4
<211> LENGTH: 41
<212> TYPE: DNA
<213> ORGANISM: Artificial Sequence
<220> FEATURE:
<223> OTHER INFORMATION: Synthetic

<400> SEQUENCE: 4
gtgtttgttc tgctcaacta atacaggtac tggtcgatga g            41

<210> SEQ ID NO 5
<211> LENGTH: 42
<212> TYPE: DNA
<213> ORGANISM: Artificial Sequence
<220> FEATURE:
<223> OTHER INFORMATION: Synthetic

<400> SEQUENCE: 5
gcagaacaaa cactccaagt tagaccacca cgcagtcaag gc           42

<210> SEQ ID NO 6
<211> LENGTH: 42
<212> TYPE: DNA
<213> ORGANISM: Artificial Sequence
<220> FEATURE:
<223> OTHER INFORMATION: Synthetic

<400> SEQUENCE: 6
gccttgactg cgtggtggtc taacttggag tgtttgttct gc           42

<210> SEQ ID NO 7
<211> LENGTH: 39
<212> TYPE: DNA
<213> ORGANISM: Artificial Sequence
<220> FEATURE:
<223> OTHER INFORMATION: Synthetic

<400> SEQUENCE: 7
caagtggaac caccacgcag tagaggcttc agttttctc              39

<210> SEQ ID NO 8
<211> LENGTH: 39
<212> TYPE: DNA
<213> ORGANISM: Artificial Sequence

```
<220> FEATURE:
<223> OTHER INFORMATION: Synthetic

<400> SEQUENCE: 8
gagaaaactg aagcctctac tgcgtggtgg ttccacttg                              39

<210> SEQ ID NO 9
<211> LENGTH: 43
<212> TYPE: DNA
<213> ORGANISM: Artificial Sequence
<220> FEATURE:
<223> OTHER INFORMATION: Synthetic

<400> SEQUENCE: 9
cagcagcgag tatcaaagac ataggcggat aacaacaaca gtg                        43

<210> SEQ ID NO 10
<211> LENGTH: 43
<212> TYPE: DNA
<213> ORGANISM: Artificial Sequence
<220> FEATURE:
<223> OTHER INFORMATION: Synthetic

<400> SEQUENCE: 10
cactgttgtt gttatccgcc tatgtctttg atactcgctg ctg                        43

<210> SEQ ID NO 11
<211> LENGTH: 40
<212> TYPE: DNA
<213> ORGANISM: Artificial Sequence
<220> FEATURE:
<223> OTHER INFORMATION: Synthetic

<400> SEQUENCE: 11
ggataacaac aacagtgaat agtcgtggac tggagctacc                            40

<210> SEQ ID NO 12
<211> LENGTH: 40
<212> TYPE: DNA
<213> ORGANISM: Artificial Sequence
<220> FEATURE:
<223> OTHER INFORMATION: Synthetic

<400> SEQUENCE: 12
ggtagctcca gtccacgact attcactgtt gttgttatcc                            40

<210> SEQ ID NO 13
<211> LENGTH: 38
<212> TYPE: DNA
<213> ORGANISM: Artificial Sequence
<220> FEATURE:
<223> OTHER INFORMATION: Synthetic

<400> SEQUENCE: 13
ggctacggag cagtatggtt aggtatctac caacctcc                              38

<210> SEQ ID NO 14
<211> LENGTH: 38
<212> TYPE: DNA
<213> ORGANISM: Artificial Sequence
<220> FEATURE:
<223> OTHER INFORMATION: Synthetic

<400> SEQUENCE: 14
ggaggttggt agatacctaa ccatactgct ccgtagcc                              38
```

<210> SEQ ID NO 15
<211> LENGTH: 40
<212> TYPE: DNA
<213> ORGANISM: Artificial Sequence
<220> FEATURE:
<223> OTHER INFORMATION: Synthetic

<400> SEQUENCE: 15
ccaacctcca gagaggcaac tagagacaag cagctaccgc                          40

<210> SEQ ID NO 16
<211> LENGTH: 40
<212> TYPE: DNA
<213> ORGANISM: Artificial Sequence
<220> FEATURE:
<223> OTHER INFORMATION: Synthetic

<400> SEQUENCE: 16
gcggtagctg cttgtctcta gttgcctctc tggaggttgg                          40

<210> SEQ ID NO 17
<211> LENGTH: 41
<212> TYPE: DNA
<213> ORGANISM: Artificial Sequence
<220> FEATURE:
<223> OTHER INFORMATION: Synthetic

<400> SEQUENCE: 17
cgaatccttc gaccaccttc taggcggcaa agtttgcttc c                        41

<210> SEQ ID NO 18
<211> LENGTH: 41
<212> TYPE: DNA
<213> ORGANISM: Artificial Sequence
<220> FEATURE:
<223> OTHER INFORMATION: Synthetic

<400> SEQUENCE: 18
ggaagcaaac tttgccgcct agaaggtggt cgaaggattc g                        41

<210> SEQ ID NO 19
<211> LENGTH: 42
<212> TYPE: DNA
<213> ORGANISM: Artificial Sequence
<220> FEATURE:
<223> OTHER INFORMATION: Synthetic

<400> SEQUENCE: 19
cacctctaca aacaaattta gagccaatca ggagcctcga ac                       42

<210> SEQ ID NO 20
<211> LENGTH: 42
<212> TYPE: DNA
<213> ORGANISM: Artificial Sequence
<220> FEATURE:
<223> OTHER INFORMATION: Synthetic

<400> SEQUENCE: 20
gttcgaggct cctgattggc tctaaatttg tttgtagagg tg                       42

<210> SEQ ID NO 21
<211> LENGTH: 40
<212> TYPE: DNA
<213> ORGANISM: Artificial Sequence
<220> FEATURE:
<223> OTHER INFORMATION: Synthetic

<400> SEQUENCE: 21
cagtatggat acctcaccct gtagaacggg agtcaggcag                              40

<210> SEQ ID NO 22
<211> LENGTH: 40
<212> TYPE: DNA
<213> ORGANISM: Artificial Sequence
<220> FEATURE:
<223> OTHER INFORMATION: Synthetic

<400> SEQUENCE: 22
ctgcctgact cccgttctac agggtgaggt atccatactg                              40

<210> SEQ ID NO 23
<211> LENGTH: 45
<212> TYPE: DNA
<213> ORGANISM: Artificial Sequence
<220> FEATURE:
<223> OTHER INFORMATION: Synthetic

<400> SEQUENCE: 23
cagtacctgt attacttgag ctagacaaac actccaagtg gaacc                        45

<210> SEQ ID NO 24
<211> LENGTH: 45
<212> TYPE: DNA
<213> ORGANISM: Artificial Sequence
<220> FEATURE:
<223> OTHER INFORMATION: Synthetic

<400> SEQUENCE: 24
ggttccactt ggagtgtttg tctagctcaa gtaatacagg tactg                        45

<210> SEQ ID NO 25
<211> LENGTH: 43
<212> TYPE: DNA
<213> ORGANISM: Artificial Sequence
<220> FEATURE:
<223> OTHER INFORMATION: Synthetic

<400> SEQUENCE: 25
ggacgatgaa gaaaagtttt agcctcagag cggggttctc atc                          43

<210> SEQ ID NO 26
<211> LENGTH: 43
<212> TYPE: DNA
<213> ORGANISM: Artificial Sequence
<220> FEATURE:
<223> OTHER INFORMATION: Synthetic

<400> SEQUENCE: 26
gatgagaacc ccgctctgag gctaaaactt ttcttcatcg tcc                          43

<210> SEQ ID NO 27
<211> LENGTH: 39
<212> TYPE: DNA
<213> ORGANISM: Artificial Sequence
<220> FEATURE:
<223> OTHER INFORMATION: Synthetic

<400> SEQUENCE: 27
ggacaaccaa tcccgtggct taggagcagt atggttctg                               39

<210> SEQ ID NO 28

```
<211> LENGTH: 39
<212> TYPE: DNA
<213> ORGANISM: Artificial Sequence
<220> FEATURE:
<223> OTHER INFORMATION: Synthetic

<400> SEQUENCE: 28
cagaaccata ctgctcctaa gccacgggat tggttgtcc                    39

<210> SEQ ID NO 29
<211> LENGTH: 38
<212> TYPE: DNA
<213> ORGANISM: Artificial Sequence
<220> FEATURE:
<223> OTHER INFORMATION: Synthetic

<400> SEQUENCE: 29
ctaccaacct ccagagaggc tagagacaag cagctacc                     38

<210> SEQ ID NO 30
<211> LENGTH: 38
<212> TYPE: DNA
<213> ORGANISM: Artificial Sequence
<220> FEATURE:
<223> OTHER INFORMATION: Synthetic

<400> SEQUENCE: 30
ggtagctgct tgtctctagc ctctctggag gttggtag                     38

<210> SEQ ID NO 31
<211> LENGTH: 23
<212> TYPE: DNA
<213> ORGANISM: Artificial Sequence
<220> FEATURE:
<223> OTHER INFORMATION: Synthetic

<400> SEQUENCE: 31
aagcagcacg acttcttcaa gtc                                     23

<210> SEQ ID NO 32
<211> LENGTH: 20
<212> TYPE: DNA
<213> ORGANISM: Artificial Sequence
<220> FEATURE:
<223> OTHER INFORMATION: Synthetic

<400> SEQUENCE: 32
tcgccctcga acttcacctc                                         20
```

US 10,087,217 B2

ADENO-ASSOCIATED VIRUS WITH SITE-DIRECTED MUTAGENESIS AND SITE-DIRECTED MODIFICATION AND PREPARATION METHOD AND APPLICATION THEREOF

This is a national stage application filed under 35 U.S.C. § 371of international application PCT/CN2014/089880, filed under the authority of the Patent Cooperation Treaty on Oct. 30, 2014, published; which claims the benefit of Patent Application No. CN 2013-10524527.X, filed on Oct. 30, 2013. The entire disclosures of all the aforementioned applications are expressly incorporated herein by reference for all purposes.

TECHNICAL FIELD

The present invention relates to an adeno-associated virus with site-directed mutagenesis and site-specific modification, specifically, the present invention relates to an adeno-associated virus with site-directed mutagenesis and site-specific modification using non-natural amino acids and adeno-associated virus capsid protein VP1 or fragment thereof. The present invention further relates to a preparation method and uses of the adeno-associated virus with site-directed mutagenesis and site-specific modification.

BACKGROUND ART

Adeno-associated viruses (AAVs) are nonenveloped, single-stranded DNA viruses of the family Parvoviridae[1] and the genus *Dependovirus* that are not associated with any known disease and show great potential as gene transfer vectors[2]. AAVs depend on co-infection with a helper virus, such as adenovirus, herpes-virus, or papillomavirus for productive replication[3]. AAV has been considered as a promising vehicle for human gene therapy based on its ability to infect both dividing and non-dividing cells, as well as establish long-term gene expression in vivo without known pathological consequence of infection[4-7]. The AAV type 2 (AAV2) nanoparticles constitutes the first primate AAV to be cloned, and promising results have been obtained with this nano vector in clinical gene transfer, including cystic fibrosis[8], retinal degenerative disorders[9-11] and haemophilia B[12, 13].

In recent years, there have been intensive efforts in many laboratories to generate targeted AAV vectors by modifying the cell-binding characteristics of these particles. The primary strategy has been to genetically modify the AAV capsid proteins by insertion of targeting peptide motifs that can direct nano vectors to specific cell types. This method has been successfully employed to retarget AAV to arterial endothelium[14], striated muscles[15], and brain vasculature[16]. However, the major technical challenges in this manipulation include the low production yield, dramatic reduction of vector titer, or significant drop of DNA packaging efficiency[17]. The large-scale genetic engineering modifications of viral capsid may abrogate their infectivity and even alter the innate interactions between viruses and host cells. For this reason, it is necessary to develop a site-selective and non-destructive technique for modifying adeno-associated viruses.

After several years of studying, comprehensive understanding of ribosome translation mechanism of prokaryotic organisms is almost achieved, crystalline and electron microscopic structures of many ribosomes under different functional status have been resolved; and structures of most aminoacyl-tRNA synthases have been obtained. On the basis of these achievements, a technology of expanding genetic code is developing in recent years, in which an amber termination codon (TAG) is used to encode a variety of non-natural amino acids and to perform site-specific incorporation into organisms in vivo. So far, this technology has been successfully used to site-specifically express dozens of non-natural amino acids in proteins of living cells, which endow these proteins with novel physical, chemical and physiological properties. By using this method, non-natural amino acids (including amino acids for affinity labeling and photoisomerization, carbonylated amino acids and glycosylated amino acids) can be incorporated into proteins (L. Wang, et al, (2001), *SCIENCE* 292:498-500; J. W. Chin, et al, 2002, *Journal of the American Chemical Society* 124: 9026-9027; J. W. Chin, &P. G. Schultz, 2002, *ChemBioChem* 11:1135-1137). These researches show that it is possible that chemical groups such as carbonyl, alkynyl and azido can be selectively and conventionally into proteins, in which these groups generally can effectively and selectively form stable covalent bonds, which is advantageous for site-specific modification of proteins and improvement of properties of proteins.

However, this technology has not been applied in site-modification of adeno-associated virus yet.

SUMMARY OF THE INVENTION

After intensive laboratory researches, the inventors surprisingly find that genetic code expanding techniques can be used to incorporate an non-natural amino acid into an adeno-associated virus capsid protein VP1 or a fragment thereof at some specific sites, which is further expressed on adeno-associated virus, thereby implementing the present invention.

In one embodiment of the present invention, 14 mutation sites are selected according to structural analysis of adeno-associated virus capsid protein VP1, the codons of amino acids corresponding to these 14 sites are mutated as TAG, and 14 VP1 protein expression vectors are constructed.

In one embodiment of the present invention, these 14 vectors are separately used with a vector comprising a gene encoding orthogonal amber mutant suppressor aminoacyl-tRNA synthase/tRNA$_{CUA}$ pairs to co-transfer cells, and non-natural amino acid NAEK is added in cell culture media. Experiments confirm that non-natural amino acid NAEK can be inserted separately at sites R447, G453, S578, N587, N587+1 and S662, while non-natural amino acid NAEK cannot be inserted at other sites. In another embodiment of the present invention, it is confirmed with experiments that non-natural amino acid DiZPK can be inserted at site N587.

The mechanism of this mutation system is that mutant tRNA$^{Pyl}$, PylRS meet the following requirements: (1) tRNA$^{Pyl}$ cannot use lysyl-tRNA enzyme of host cell, and can be acylated by mutant Py1RS only; (2) mutant Py1RS can acylate tRNAPy1 only, and cannot acylate other tRNA; that is, mutant tRNAPy1 and Py1RS have an orthogonal relation between each other. This orthogonal enzyme, and only this enzyme, can acylate an non-natural amino acid to this orthogonal tRNA, and to only this tRNA, but cannot acylate other tRNA. The resultant orthogonal lysyl-tRNA synthase/tRNA system makes NAEK or DiZPK, which are not 20 common amino acids, to correspond to amber codon TAG, so that this non-natural amino acid is incorporated into adeno capsid protein.

In one embodiment of the present invention, an adeno-associated virus with a site-specifically inserted non-natural amino acid is obtained.

In embodiments of the present invention, an adeno-associated virus with a site-specific mutation is equivalent to a wild-type virus in terms of viral production and transduction ability to cell.

In embodiments of the present invention, an adeno-associated virus with a site-specific mutation is co-incubated with a fluorescence labeling molecule, so that an non-natural amino acid is coupled to the fluorescence labeling molecule via a click chemistry.

In one embodiment of the present invention, a motion trail of single virus can be observed under a confocal microscopy via a fluorescence labeling molecule coupled with an adeno-associated virus with a site-specific mutation.

In one embodiment of the present invention, an adeno-associated virus with site-specific mutation is coupled to a targeting molecule via a click chemistry, which can improve targeting ability of an adeno-associated virus with site-specific mutation to a cell.

In one embodiment of the present invention, an adeno-associated virus with site-specific mutation can further express a functional protein or a nucleic acid, so that the functional protein or the nucleic acid can exert activity in an infected cell.

More specifically, the present invention relates to the following aspects.

The first aspect of the present invention relates to a site-specifically mutated adeno-associated virus capsid protein VP1 or a fragment thereof, in which an amino acid at a specific site of a corresponding wild type adeno-associated virus capsid protein VP1 or a fragment thereof is mutated as an non-natural amino acid, the specific site is at least one site selected from sites R447, G453, S578, N587, N587+1, S662 of VP1 or fragment thereof.

In embodiments of the present invention, the VP1 has an amino acid sequence as shown in SEQ ID NO: 1, and the VP1 has a nucleotide sequence as shown in SEQ ID NO: 2.

The adeno-associated virus capsid protein VP1 or fragment thereof according to any one of items of the first aspect of the present invention, in which the non-natural amino acid for example can be an azido non-natural amino acid, a photo-crosslinking non-natural amino acid, a keto non-natural amino acid, an alkynyl non-natural amino acid, an acetyl non-natural amino acid, a phosphoryl non-natural amino acid, a methyl non-natural amino acid. In embodiments of the present invention, the non-natural amino acid is an azido-containing non-natural amino acid, for example, Nε-2-azideoethyloxycarbonyl-L-lysine (NAEK),

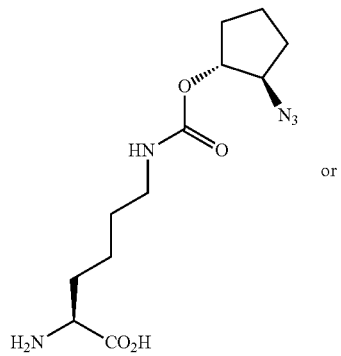

or

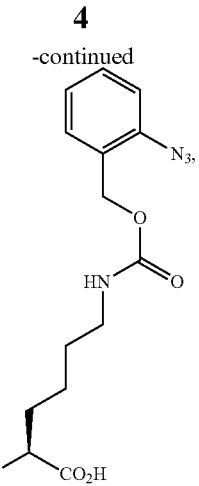

or the non-natural amino acid is an non-natural amino acid with structure similar to the above azido-containing non-natural amino acid, for example, DiZPK.

In one embodiment of the present invention, an amino acid at a specific site of a wild type adeno-associated virus capsid protein VP1 or fragment thereof is mutated as NAEK, the specific site is at least one site selected from sites R447, G453, S578, N587, N587+1, S662 of the VP1 or fragment thereof.

In another embodiment of the present invention, an amino acid at a specific site of a wild type adeno-associated virus capsid protein VP1 or fragment thereof is mutated as DiZPK, the specific site is site N587 of the VP1 or fragment thereof.

The adeno-associated virus capsid protein VP1 or fragment thereof according to any one of items of the first aspect of the present invention, in which the NAEK and the amino acid sequence of VP1 or fragment thereof are linked in a manner as shown in Formula I:

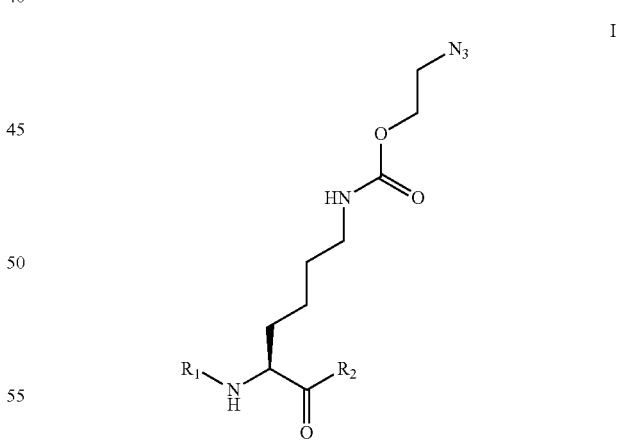

wherein the direction from R1 to R2 is the direction from N-terminal to C-terminal of the amino acid sequence, in which amino acid at site N is one of amino acids at sites selected from site R447, site G453, site S578, site N587, site N587+1, site S662, R1 is an amino acid residue at site 1 to site N−1 of the amino acid sequence of VP1 or fragment thereof, R2 is an amino acid residue at site N+1 to C-terminal of the amino acid sequence of VP1 or fragment thereof.

The adeno-associated virus capsid protein VP1 or fragment thereof according to any one of items of the first aspect of the present invention, in which the DiZPK and the amino acid sequence of VP1 or fragment thereof are linked in a manner as shown in Formula II:

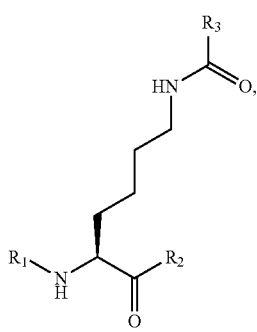

wherein the direction from R1 to R2 is the direction from N-terminal to C-terminal of the amino acid sequence, in which amino acid at site N is amino acid at site N587, R1 is an amino acid residue at site 1 to site N−1 of the amino acid sequence of VP1 protein or fragment thereof, R2 is an amino acid residue at site N+1 to C-terminal of the amino acid sequence of VP1 protein or fragment thereof, R3 is

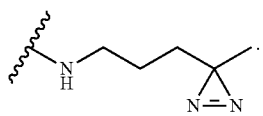 [SMILES: *NCCCC1(C)N=N1]

The adeno-associated virus capsid protein VP1 or fragment thereof according to any one of items of the first aspect of the present invention, in which the adeno-associated virus is type 2 adeno-associated virus (AAV2).

The adeno-associated virus capsid protein VP1 or fragment thereof according to any one of items of the first aspect of the present invention, in which the non-natural amino acid further links to a labeling group, such as fluorescence labeling group, or a labeling group capable of occurring a click chemistry with azide.

In embodiments of the present invention, the labeling group is Alexa fluorescence group, such as Alexa 488 or Alexa 555. In some specific embodiments, the labeling group is DIBO-Alexa 488 or DIBO-Alexa 555.

In embodiments of the present invention, a DIBO-containing labeling molecule is linked to an azido-containing non-natural amino acid via a click chemistry, especially a copper-free click chemistry.

The adeno-associated virus capsid protein VP1 or fragment thereof according to any one of items of the first aspect of the present invention, in which the non-natural amino acid further links to another functional molecule, such as targeting molecule, preferably, the targeting molecule further links to a group capable of occurring click chemistry with an azide, such as DIBO (dibenzocyclooctyne), cyclooctyne, alkynyl.

The second aspect of the present invention relates to a site-specifically mutated adeno-associated virus capsid protein, which comprises the adeno-associated virus capsid protein VP1 or fragment thereof according to any one of items of the first aspect of the present invention.

The third aspect of the present invention relates to a site-specifically mutated adeno-associated virus, which comprises the adeno-associated virus capsid protein VP1 or fragment thereof according to any one of items of the first aspect of the present invention, or the adeno-associated virus capsid protein according to any one of items of the second aspect.

The adeno-associated virus according to any one of items of the third aspect according to the present invention, wherein the non-natural amino acid further links to a labeling group, such as fluorescence labeling group, or a labeling group capable of occurring a click chemistry with azide.

In embodiments of the present invention, the labeling group is Alexa fluorescence group, such as Alexa 488 or Alexa 555. In some specific embodiments, the labeling group is DIBO-Alexa 488 or DIBO-Alexa 555.

In embodiments of the present invention, a DIBO-containing labeling molecule is linked to an azido-containing non-natural amino acid via a click chemistry, especially a copper-free click chemistry.

The adeno-associated virus according to any one of items of the third aspect according to the present invention, wherein the non-natural amino acid further links to another functional molecule, such as targeting molecule, preferably, the targeting molecule further links to a group capable of occurring click chemistry with an azide, such as DIBO (dibenzocyclooctyne), cyclooctyne, alkynyl.

In the present invention, the targeting molecules include any molecules having targeting function known in the prior art, which are substances capable of targeting cells, tissues or organs, for example, which may refer to substances capable of specifically binding to proteins or nucleic acids (e.g., epidermal growth factor receptors, epidermal growth factor receptor tyrosine kinases, vascular endothelial growth factor receptors, leukocyte differentiation antigens, integrins, acetylcholine receptors, folate receptors) on surface or in cellular internal (e.g., specific subcellular fractions or organelles) of a kind or group of specific cells (e.g., tumor cells, immune cells), and the targeting molecules can be for example antigens, ligands, signal peptides, toxins, nucleic acids, polysaccharides, folic acids, etc. The targeting molecule can additionally promote a fraction to which it links enters a target cell, tissue or organ.

In embodiments of the present invention, the targeting molecules refer to molecules capable of targeting tumor cell surface proteins, such as molecules capable of binding to integrins on tumor cell surface, for example, RGD, especially cyclic RGD.

The adeno-associated virus according to any one of items of the third aspect according to the present invention, which carries a functional nucleic acid fragment or a nucleic acid fragment of a labeling molecule.

In the present invention, the functional nucleic acid fragment can act as a functional protein or nucleic acid in a cell, a tissue or an organ, wherein the functional protein is a protein having activity on the cell, tissue or organ well known in the art, for example, a cytotoxin, a tumor necrosis factor, an apoptosis-promoting protein, a growth hormone, an interferon, a neurotrophic factor, and the functional nucleic acid is a nucleic acid molecule have activity as well known in the art, for example, a RNA molecule, such as small interfering RNA, micro-RNA, etc.

In the present invention, the labeling molecule is a molecule having labeling function as well known in the art, for example, a fluorescence molecule, a polypeptide, an antibody, an enzyme, a functional small molecular compound, etc.

In embodiments of the present invention, the functional nucleic acid fragment refers to a nucleic acid fragment encoding an apoptosis-inducing ligand associated with thymidine kinase or tumor necrosis factor.

In embodiments of the present invention, the nucleic acid fragment of the labeling molecule refers to a nucleic acid fragment encoding GFP.

The forth aspect of the present invention relates to a nucleic acid encoding the adeno-associated virus capsid protein VP1 or fragment thereof according to any one of items of the first aspect of the present invention, the nucleic acid differs from a nucleic acid encoding a corresponding wild type adeno-associated virus capsid protein in that the codon encoding the non-natural amino acid at the specific site amino acid is TAG.

In one embodiment of the present invention, wherein the codon encoding one amino acid of the amino acids at sites R447, G453, S578, N587, N587+1, S662 of a wild type adeno-associated virus capsid protein VP1 or fragment thereof is mutated as TAG.

In another embodiment of the present invention, wherein the codon encoding the amino acid at site N587 of a wild type adeno-associated virus capsid protein VP1 or fragment thereof is mutated as TAG.

The fifth aspect of the present invention relates to a nucleic acid vector, which operably links to the nucleic acid molecule according to any one of items of the forth aspect of the present invention.

The nucleic acid vector according to any one of items of the fifth aspect of the present invention, wherein the vector is a eukaryotic expression vector or an adeno-associated virus vector.

In one embodiment of the present invention, which is vector pCMV-VP1-Flag operably linking to the nucleic acid molecule acid molecule according to any one of items of the forth aspect of the present invention.

In one embodiment of the present invention, which is vector pAAV-RC in which the codon encoding one amino acid of the amino acids at sites R447, G453, S578, N587, N587+1, S662 of a wild type adeno-associated virus capsid protein VP1 or fragment thereof is mutated as TAG.

The present invention further relates to a host cell, which comprises the nucleic acid vector according to any one items of the fifth aspect of the present invention.

The host cell according to any one of items of the present invention, further comprises a vector of gene encoding orthogonal amber mutant suppressor aminoacyl-tRNA synthase/$tRNA_{CUA}$ pairs.

In embodiments of the present invention, the vector of gene encoding orthogonal amber mutant suppressor aminoacyl-tRNA synthase/$tRNA_{CUA}$ is a plasmid pACYC-tRNA/Py1RS, which is obtained from pACYC-tRNA/Py1RS of *Escherichia coli* with deposition date of Jun. 14, 2011 and deposition number of CGMCC No: 4951.

The host cell according to any one of items of the present invention, further comprises a pHelper vector and a pAAV-GFP vector.

In embodiments of the present invention, the host cell is a cell of mammal, the mammal is human, monkey, mouse, bovine, equine, caprine, etc.

In embodiments of the present invention, the host cell is AAV-293 cell.

In another embodiment of the present invention, the host cell is HeLa cell.

In another embodiment of the present invention, the host cell is U87 cell.

The present invention further relates to a method for preparing a site-specifically mutated adeno-associated virus capsid protein VP1, VP2 or VP3, which comprises the following steps:

(1) cloning a gene of a wild type VP1 protein into a suitable expression vector to obtain a recombinant expression vector;

(2) selecting one or more specific amino acid sites from amino acid sequence of a wild type adeno-associated virus capsid protein VP1 or fragment thereof, preferably, selecting the specific amino acid sites from sites R447, G453, S578, N587, N587+1, S662 of VP1 or fragment thereof;

(3) mutating a codon in the recombination expression vector, which encodes the amino acid of VP1 or fragment thereof at the site selected in step (2), as codon TAG by a genetic engineering method, to obtain a mutant sequence expression vector of the site-specifically mutated VP1 or fragment thereof;

(4) co-transfecting a suitable host cell with the mutant sequence expression vector as obtained in step (3) and a vector of gene encoding orthogonal amber mutant suppressor aminoacyl-tRNA synthase/$tRNA_{CUA}$ pairs, culturing the successfully co-transfected host cell in a culture media comprising an non-natural amino acid, inducing expression under suitable conditions, to obtain the site-specifically mutated adeno-associated virus capsid protein VP1 or fragment thereof.

In one embodiment of the present invention, the specific amino acid site is one site selected from sites R447, G453, S578, N587, N587+1, S662 of VP1 or fragment thereof.

In another embodiment of the present invention, the specific amino acid site is site N587 of VP1 or fragment thereof.

In embodiments of the present invention, the suitable vector is eukaryotic expression vector, such as vector pCMV-VP1-flag.

In embodiments of the present invention, the mutant sequence expression vector is pCMV-VP1-flag-R447, pCMV-VP1-flag-G453, pCMV-VP1-flag-S578, pCMV-VP1-flag-N587, pCMV-VP1-flag-N587+1 or pCMV-VP1-flag-S662.

In embodiments of the present invention, the vector of gene encoding orthogonal amber mutant suppressor aminoacyl-tRNA synthase/$tRNA_{CUA}$ is a plasmid pACYC-tRNA/Py1RS, which is obtained from pACYC-tRNA/Py1RS of *Escherichia coli* with deposition date of Jun. 14, 2011 and deposition number of CGMCC No: 4951.

In embodiments of the present invention, the vector co-transfected in step (4) further comprises vectors pHelper and pAAV-GFP.

In embodiments of the present invention, the suitable host cell in step (4) is an AAV-293 incasing cell.

In embodiments of the present invention, the non-natural amino acid an azido-containing non-natural amino acid, for example, Nε-2-azideoethyloxycarbonyl-L-lysine (NAEK), or the non-natural amino acid is an non-natural amino acid with structure similar to the above azido-containing non-natural amino acid, for example, DiZPK.

In embodiments of the present invention, the successfully transfected host cell is cultured in a culturing media comprising 1 mM of non-natural amino acid for 48 h.

The present inventor further relates to a method for preparing a site-specifically mutated adeno-associated virus, which comprises the following steps:

(1) providing a plasmid pAAV-RC (which contains a gene encoding capsid protein VP1, VP2 or VP3) for virus packaging, selecting one or more specific amino acid sites to be mutated from amino acid sequence of a wild-type adeno-associated virus capsid protein VP1 or fragment thereof, preferably, the specific amino acid site is at least one site selected from sites R447, G453, S578, N587, N587+1, S662 of VP1 or fragment thereof;

(2) using the plasmid pAAV-RC of step (1) as template, mutating a codon, which encodes the amino acid of VP1 or fragment thereof at the site selected in step (1), as codon TAG by a genetic engineering method, to obtain a site-specifically mutated virus packaging plasmid;

(3) co-transfecting a host cell with the mutant sequence expression vector obtained in step (3) and a vector of gene encoding orthogonal amber mutant suppressor aminoacyl-tRNA synthase/tRNA$_{CUA}$ pairs, culturing the successfully co-transfected host cell in a culture media comprising an non-natural amino acid, inducing expression under suitable conditions, to obtain the site-specifically mutated adeno-associated virus.

In one embodiment of the present invention, the specific amino acid site is one site selected from sites R447, G453, S578, N587, N587+1, S662 of VP1 or fragment thereof.

In another embodiment of the present invention, the specific amino acid site is site N587 of VP1 or fragment thereof.

In embodiments of the present invention, the mutant sequence expression vector is pAAV-RC-R447, pAAV-RC-G453, pAAV-RC-S578, pAAV-RC-N587, pAAV-RC-N587+1 or pAAV-RC-S662.

In embodiments of the present invention, the vector of gene encoding orthogonal amber mutant suppressor aminoacyl-tRNA synthase/tRNA$_{CUA}$ is a plasmid pACYC-tRNA/PylRS, which is obtained from pACYC-tRNA/PylRS of *Escherichia coli* with deposition date of Jun. 14, 2011 and deposition number of CGMCC No: 4951.

In embodiments of the present invention, the vector co-transfected in step (4) further comprises vectors pHelper and pAAV-GFP.

In embodiments of the present invention, the suitable host cell in step (4) is an AAV-293 incasing cell.

In embodiments of the present invention, the non-natural amino acid is NAEK or DiZPK.

In embodiments of the present invention, the successfully transfected host cell is cultured in a culturing media comprising 1 mM of non-natural amino acid for 72 h.

The present invention further relates to a composition (e.g., pharmaceutical composition) or a kit, which comprises the adeno-associated virus according to any one of items of the third aspect of the present invention, or the nucleic acid molecule according to any one of items of the forth aspect, or the nucleic acid vector according to any one of items of the fifth aspect, and optional pharmaceutically acceptable excipients.

The present invention further relates to a gene vaccine, which comprises the adeno-associated virus according to any one of items of the third aspect of the present invention, or the nucleic acid molecule according to any one of items of the forth aspect, or the nucleic acid vector according to any one of items of the fifth aspect.

The present invention further relates to a use of the adeno-associated virus according to any one of items of the third aspect of the present invention, or the nucleic acid molecule according to any one of items of the forth aspect, or the nucleic acid vector according to any one of items of the fifth aspect, in manufacture of a preparation for obtaining adeno-associated virus binding protein, or in manufacture of a medicament for gene therapy, or in manufacture of a DNA vaccine.

The present invention further relates to a use of the adeno-associated virus according to any one of items of the third aspect of the present invention as a tool adeno-associated virus.

In the present invention, the adeno-associated virus can be used as a tool viral vector, which can carry a functional gene corresponding to specific requirement or couple to a functional molecule on surface thereof, and be used for fundamental researches, gene therapy or manufacture of DNA vaccine.

The present invention further relates to a gene therapeutic method, the method comprising administering a subject in need with an effective amount of the adeno-associated virus according to any one of items of the third aspect of the present invention, or the nucleic acid molecule according to any one of items of the forth aspect, or the nucleic acid vector according to any one of items of the fifth aspect.

In embodiments of the present invention, a targeting molecule is coupled to surface of adeno-associated virus with site-specific mutation and modification, and the adeno-associated virus also expresses functional protein at the same time, the adeno-associated virus can be targeted to a specific cell by using the targeting molecule, the functional protein specifically exerts activity to the specific cell, so as to fulfill gene therapy.

In embodiments of the present invention, a targeting molecule cyclic RGD is coupled to surface of adeno-associated virus with site-specific mutation and modification, and the adeno-associated virus also expresses functional protein TNF-related apoptosis-inducing ligand or thymidine kinase at the same time, the adeno-associated virus can be targeted to a tumor cell expressing high level of integrin by using the targeting molecule, the functional protein specifically exerts activity to the tumor cell, so as to fulfill gene therapy.

In the present invention, the adeno-associated virus can be adeno-associated viruses of various serotypes, for example, can be AAV1, AAV2, AAV5, AAV6, AAV7, AAV8, AAV9. In embodiments of the present invention, the adeno-associated virus is AAV2. When using adeno-associated virus of other serotypes, those skilled in the art well know that a plasmid comprising an encoding sequence of corresponding capsid protein can be selected for a different viral capsid protein.

In the present invention, the adeno-associated virus and adeno-associated virus vector have the same meaning.

In the present invention, the mutated amino acid sites of VP1 are all based on VP1 of type AAV2 adeno-associated virus standard strain (which amino acid sequence is shown in SEQ ID NO:1); if adenoviruses of other types are used, those skilled in the art can obtain sites corresponding to mutation sites R447, G453, S578, N587, N587+1, S662 of the present invention according to amino acid sequences of other types adenovirus VP1.

In the present invention, the fragment of VP1 refers to a protein formed with part of sequence of VP1, especially a protein formed with its C-terminal sequence, for example, which refers to capsid protein VP2 or capsid protein VP3; wherein VP2 is a protein formed with 598 amino acids at C-terminal of VP1, VP3 is a protein formed with 533 amino acids at C-terminal of VP1.

In the present invention, the amino acid sites of the fragment of VP1 are defined like those of VP1; for example, the amino acid at site R447 of VP2 as mentioned in the present invention corresponds to the amino acid at actual site R310 of VP2.

In the present invention, when adeno-associated virus VP1 or fragment thereof is mentioned, it is described by the sequence as shown in SEQ ID NO: 1. For example, expression "amino acid at site R447 of VP1 or fragment thereof" refers to the amino acid residue at site R447 of the polypeptide as shown in SEQ ID NO: 1. However, those skilled in the art would understand that the amino acid sequence of adeno-associated virus VP1 may have naturally generated or artificially introduced mutations or variations (including, but not being limited to, replacement, deficiency and/or addition, for example, various serotypes or chimeric serotypes of adeno-associated virus VP1 or fragments thereof or mutants thereof), with proviso that its biological functions are not influenced. Hence, in the present invention, the term "VP1 or fragment thereof" should include all of these sequences, for example, include the sequence as shown in SEQ ID NO: 1 and its natural or artificial variants. In addition, when fragment of VP1 sequence is mentioned, it not only includes the fragments of SEQ ID NO: 1, but also includes corresponding fragments of sequences of natural or artificial variants of VP1. For example, the expression "amino acid at site R447 of VP1" refers to the amino acid residue at site R447 of SEQ ID NO: 1, and corresponding amino acid residues of its (natural or artificial) variants. According to the present invention, the expression "corresponding site" refers to sites at equivalent positions of sequences in an optimum comparison for obtaining the highest percentage of identity.

In the present invention, the algorithm used for determine sequence identity and sequence similarity is for example, BLAST or BLAST 2.0 algorithm, they are separately described by Altschul, et al, (1977) Nucl. Acid. Res. 25: 3389-3402, and Altschul, et al, (1990) J. Mol. Biol. 215: 403-410. When using parameters of the references or default parameters, BLAST and BLAST 2.0 can be used to determine the identity percentage of amino acid sequence of the present invention. The software for executing BLAST analysis can be obtained by public from the National Center of Biotechnology Information.

In the present invention, the amino acid sequences having at least 90% sequence identity in comparison with the amino acid sequence include polypeptide sequences substantively identical to the amino acid sequence. For example, when the method of the present invention (e.g., BLAST analysis with standard parameters) is used, these sequences have at least 90% sequence identity, preferably at least 91%, 92%, 93%, 94%, 95%, 96%, 97%, 98% or 99% or higher sequence identity, in comparison with the polypeptide sequence of the present invention.

In embodiments of the present invention, the type AAV2 adeno-associated virus refers to a type AAV2 adeno-associated virus standard strain, which has an amino acid sequence of VP1 as shown in SEQ ID NO: 1.

In the present invention, the adeno-associated virus capsid protein is encoded by adeno-associated virus cap gene, which separately encodes 3 structural proteins VP1, VP2 and VP3, with molecular weights of 87, 73, 61 kDa, respectively.

In the present invention, the non-natural amino acid can be any non-natural amino acids known in the prior art, for example, an azido non-natural amino acid, a photo-cross-linking non-natural amino acid, a keto non-natural amino acid, an alkynyl non-natural amino acid, an acetyl non-natural amino acid, a phosphoryl non-natural amino acid, a methyl non-natural amino acid, which meanings can be seen in references [21], [22].

In the present invention, the gene therapy refers to a method in which an exogenous gene is inserted in a suitable target cell by gene transfer techniques so that a product generated by the exogenous gene can be used to treat a disease. Generally, the gene therapy may further comprise means and techniques used under DNA levels for treatment of some diseases.

In the present invention, the DNA vaccine is also called as nucleic acid vaccine or gene vaccine, and refers to a eukaryotic expression plasmid DNA (may also be RNA in some cases) or viral expression vector (e.g., adeno-associated virus vector) encoding an immunogen or an immunogen-associated protein, which can enter an animal body via a certain route, after being uptaking by host cells, transcript and translate to express the immunogen or immunogen-associated protein, and the protein can stimulate the body to generate non-specific and/or specific immune response, thereby exerting immune protection function.

In the present invention, the N587+1 refers to inserting an non-natural amino acid between N587 and R588; when constructing the expression plasmid, TAG is inserted between codons of N587 and R588; N450+1, N385+1 have similar meanings.

In the present invention, the adeno-associated viruses with specific mutation and modification of non-natural amino acids are equivalent to wild-type adeno-associated virus in terms of production, transfection, movement and transportation, and it is confirmed that they can be used to improve transduction efficiency and normally carry a functional gene by further coupling the non-natural amino acids to other functional molecules such as targeting molecules, which indicates that the site-specifically mutated adeno-associated viruses can be used as tool adeno-associated viruses, and used for finding adeno-associated virus binding proteins or as targeting gene therapy carriers as well as in various fields relating to adeno-associated viruses.

A refers to that AAV2 particle can be site-specifically modified by genetically coded azido-containing amino acid NAEK; B refers to that it can be tagged with a fluorescence molecule via biological orthogonal reaction.

Figure 2:
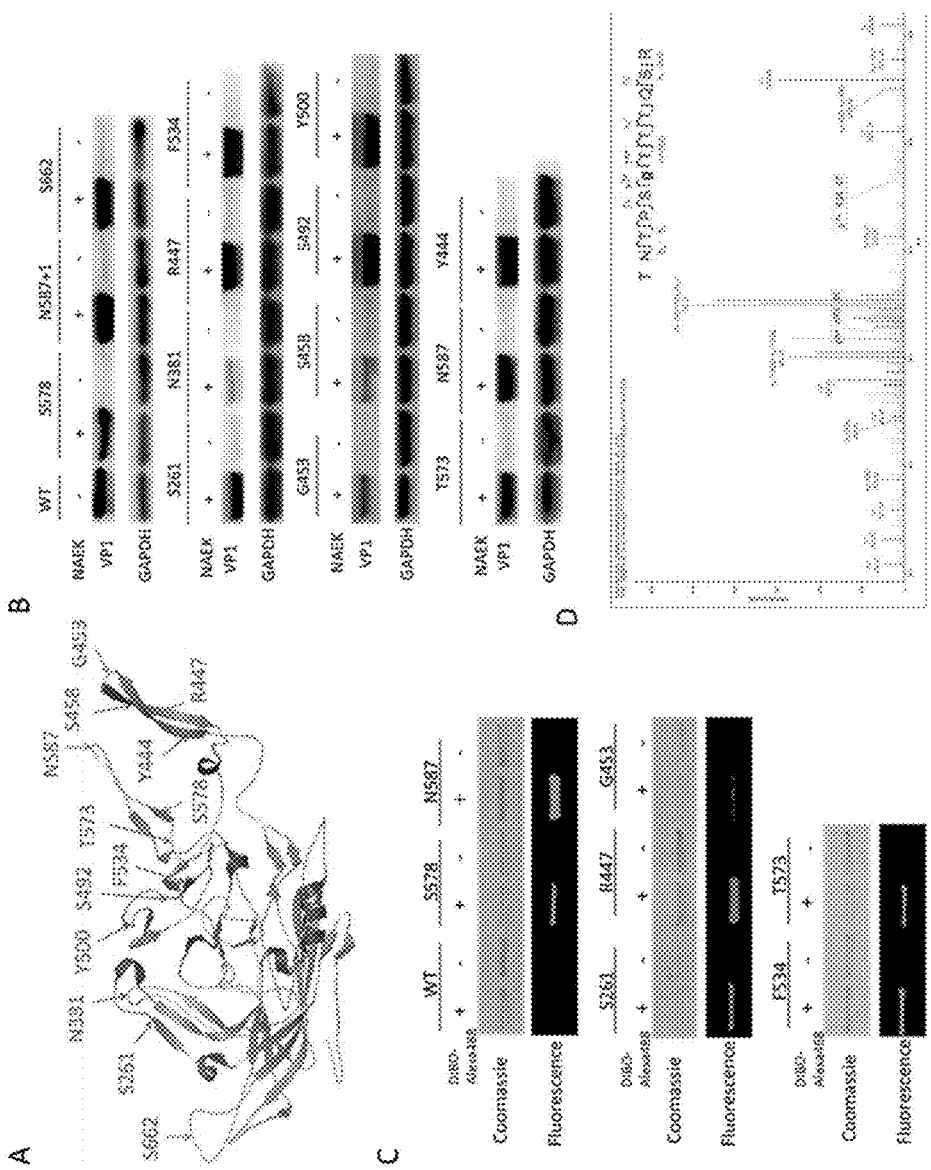

FIG. 2 shows that NAEK can be effectively and genetically inserted in AAV capsid protein VP1;

A, selection of site for inserting NAEK into VP1;

B, amber termination codon-carrying NAEK-dependent VP1 expression separately at 14 sites;

C, Coomassie brilliant blue stain and intramicellar fluorescein stain of DIBO-Alexa488-tagged VP1 protein, in which coupling depends on NAEK presentation on VP1 surface.

D, MS/MS fragment spectrum of purified and trypsinized $VP1^{G453NAEK}$, in which the site of NAEK is labeled with g.

Figure 3:
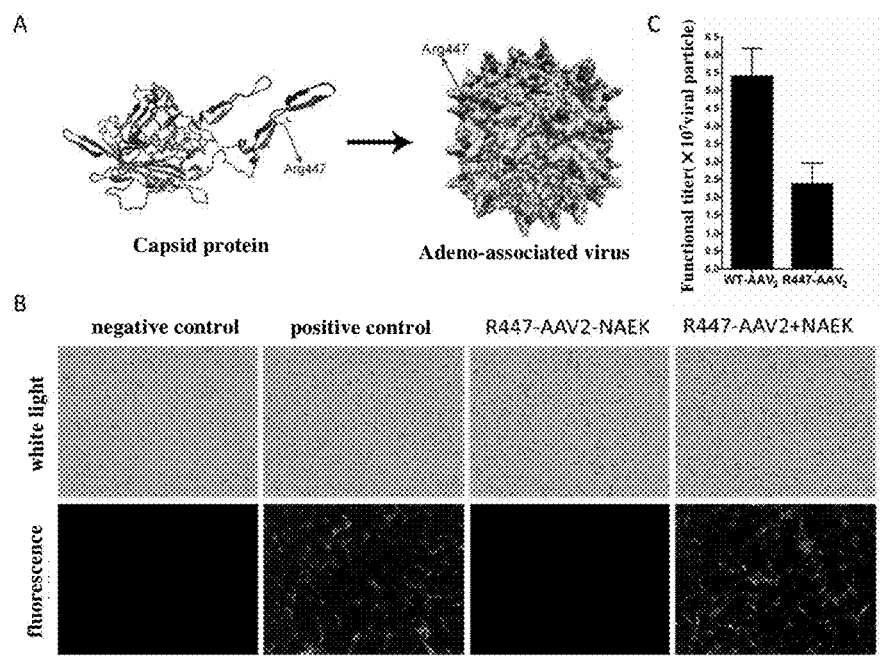

FIG. 3 shows that AAV2 particle can be site-specifically tagged with a genetically encoded azido label;

A shows a diagrammatic figures of main capsid protein and viral capsid of AAV2 obtained by atomic structure (from protein database) of Xie, et al, in which the inserted Arg447 site (red) is labeled;

B shows GFP expression results detected after 48 h of transfection with virus extracts of AAV-293 incasing cells which are cultured by transfecting HT-1080 cells then adding (+) or not adding (−) NAEK, in which proportional scale is equivalent to 100 μm;

C shows calculated virus titers of HT-1080 cells transfected with a series of diluted rAAVr, in which error bar represents a standard deviation of mean of 3 tests, and ordinate represents functional titer ($\times 10^7$ virus particles/ml).

Figure 4:
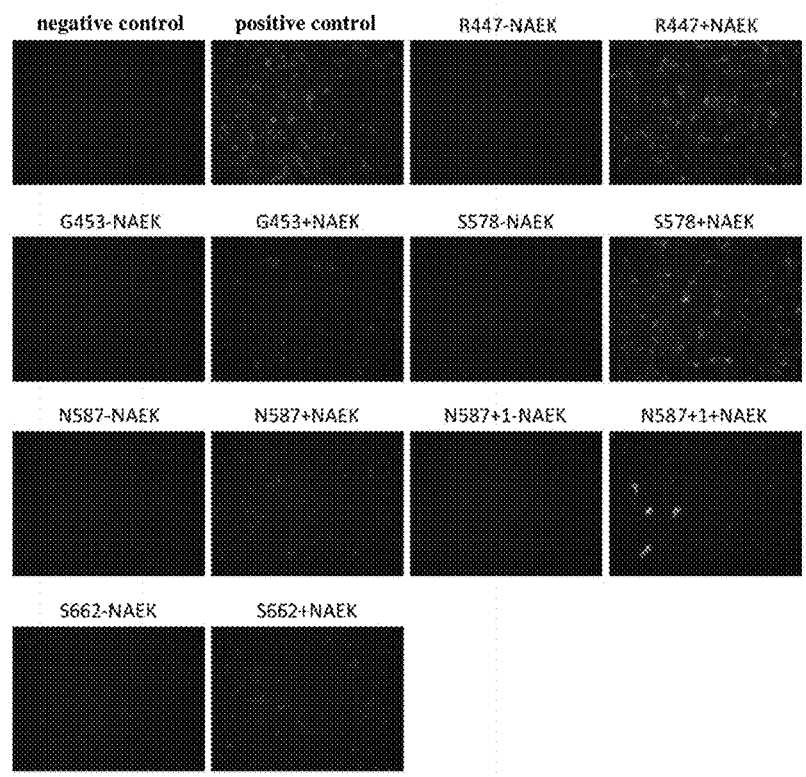

FIG. 4 shows NAEK is successfully inserted at different sites of AAV2 capsid;

Mutant virus generated on basis of NAEK are co-cultured with HT-1080 cells for 48 h, and GFP expression is reported if the mutant virus is successfully transferred into HT-1080 cells; the results show that R447-AAV2 and S568-AAV2 are substantially equivalent to wild-type virus in viral infectivity.

Figure 5:
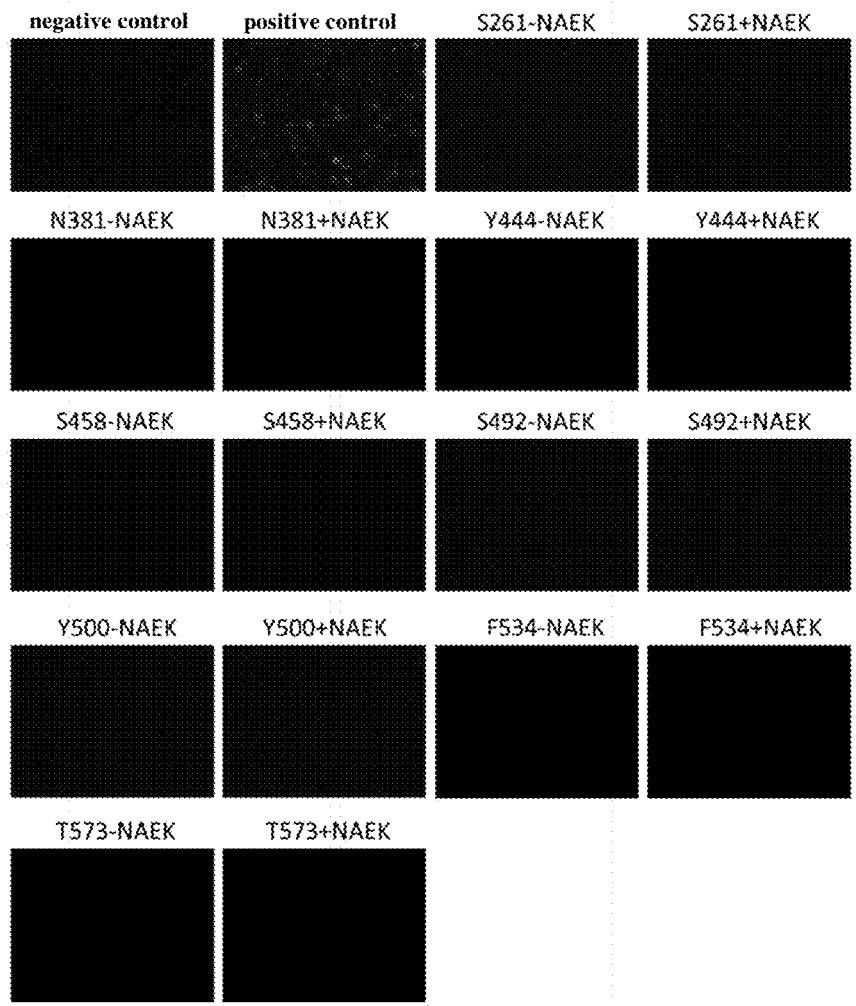

FIG. 5 shows NAEK cannot be inserted into AAV2 at some sites.

Figure 6:
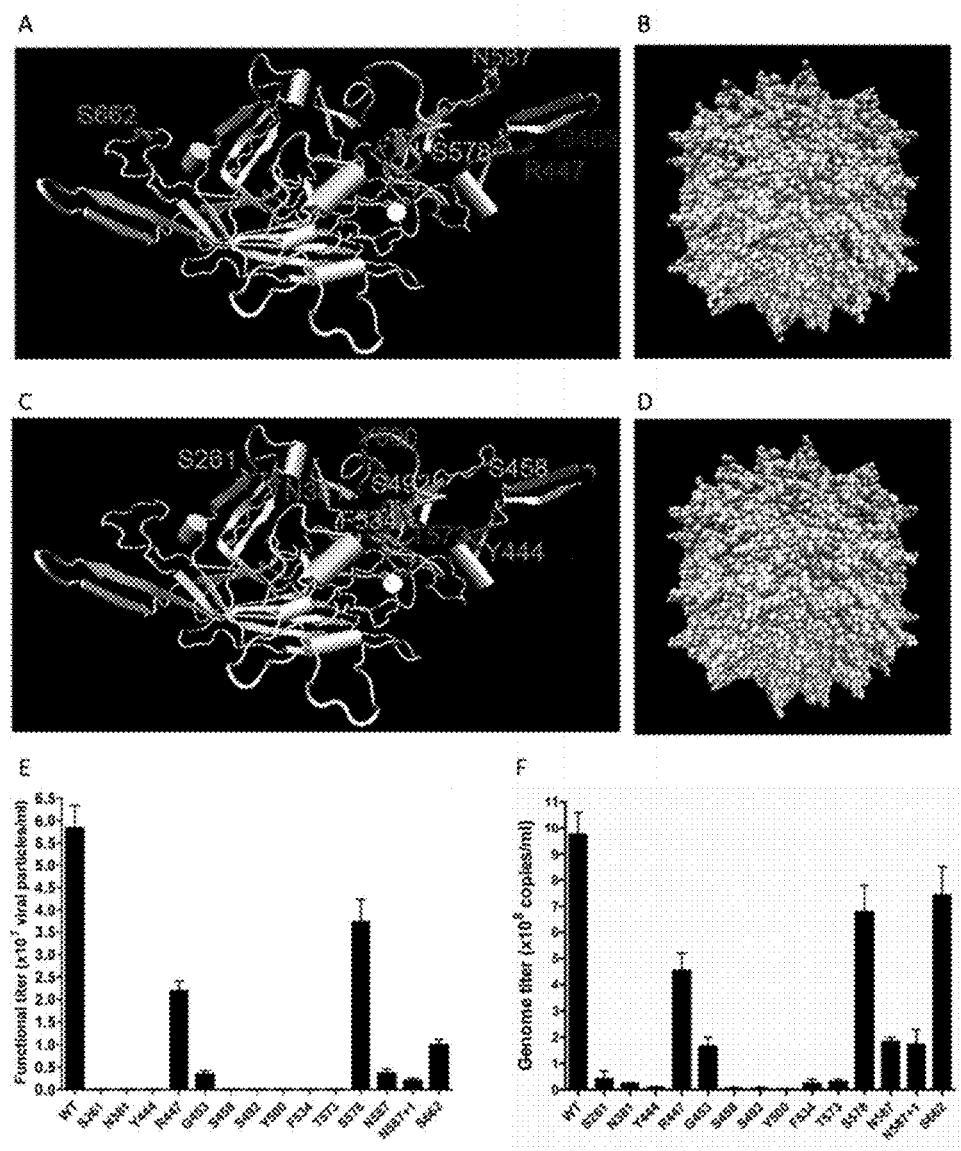

FIG. 6 shows AAV2-GFP virus particles can be site-specifically tagged by a genetically encoded NAEK label.

A and B show mode patterns of main AAV2 capsid protein and AAV2 virus particles; AAV2-GFP can be successfully mutated at sites R447, G453, S578, N587, S662 with an amino acid-carrying adize compound (NAEK).

C and D show that AAV2-GFP cannot be mutated at sites S261, N381, Y444, S458, S492, Y500, F534, T573.

E shows the calculated viral titers of HT-1080 cells transduced with a serially diluted AAV2-GFP, in which error bar represents a standard deviation of mean of 3 repeated tests.

F shows GFP quantitation via Q-PCR using genome titers of AAV2-GFP incorporated at different sites with NAEK.

Figure 7:
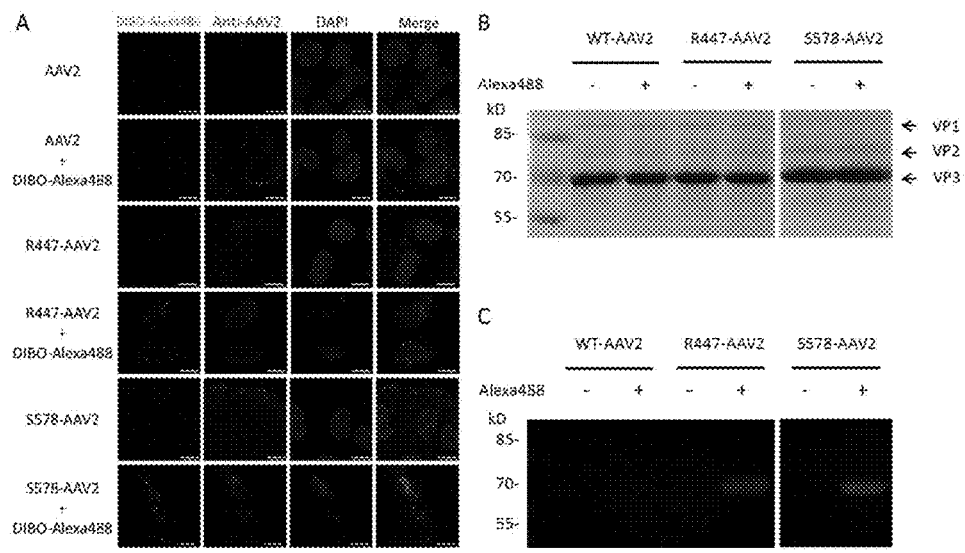

FIG. 7 shows viral surface is successfully modified with Alexa 488;

A shows fluorescence tagged NAEK; wild-type virus (WT AAV2), NAEK-tagged virus (R447-AAV2) particles and S578-AAV2 virus particles are co-cultured at 37° C. for 30 min with Hela cells in which DIBO-Alexa 488 (green) is added or not, then fixed, permeabilized, and immune stained (red) with mouse monoclonal antibody (A20 clone) for integral AAV2; the azido tag (green) and R447-AAV2 particles (red) for labeling are co-localized; overlapped green and red signals show a yellow color of fused images; AAV2 in first row is not co-cultured with A20 antibody, and used as negative control; and proportional scale is equivalent to 10 μm.

B and C show that AAV reacted or unreacted with DIBO-Alexa 488 is detected by SDS-PAGE, in which Alexa 488 (C) is detected by 488 nm transmission light, and then gel is stained with Coomassie brilliant blue (B).

Figure 8:
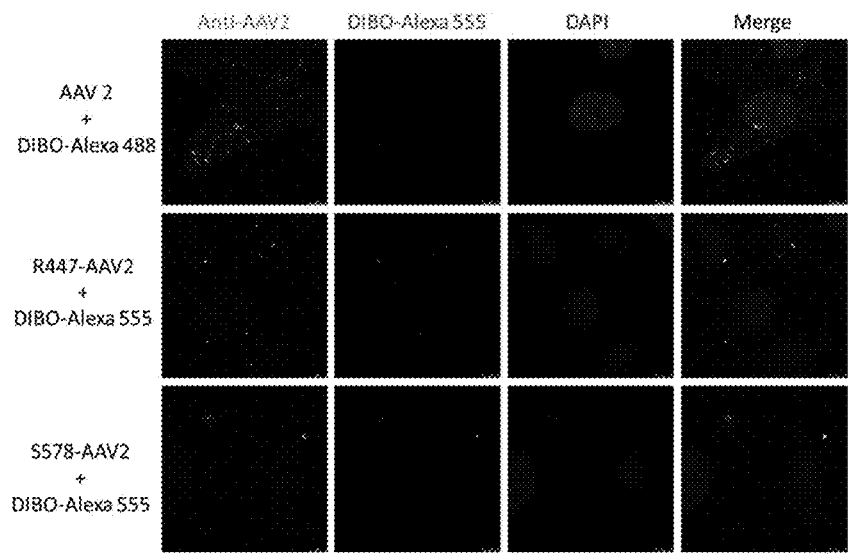

FIG. 8 shows results of confocal microscopy that Alexa 555 is also successfully links to AAV2 via NAEK at sites R447 and S578 of capsid protein.

Figure 9:
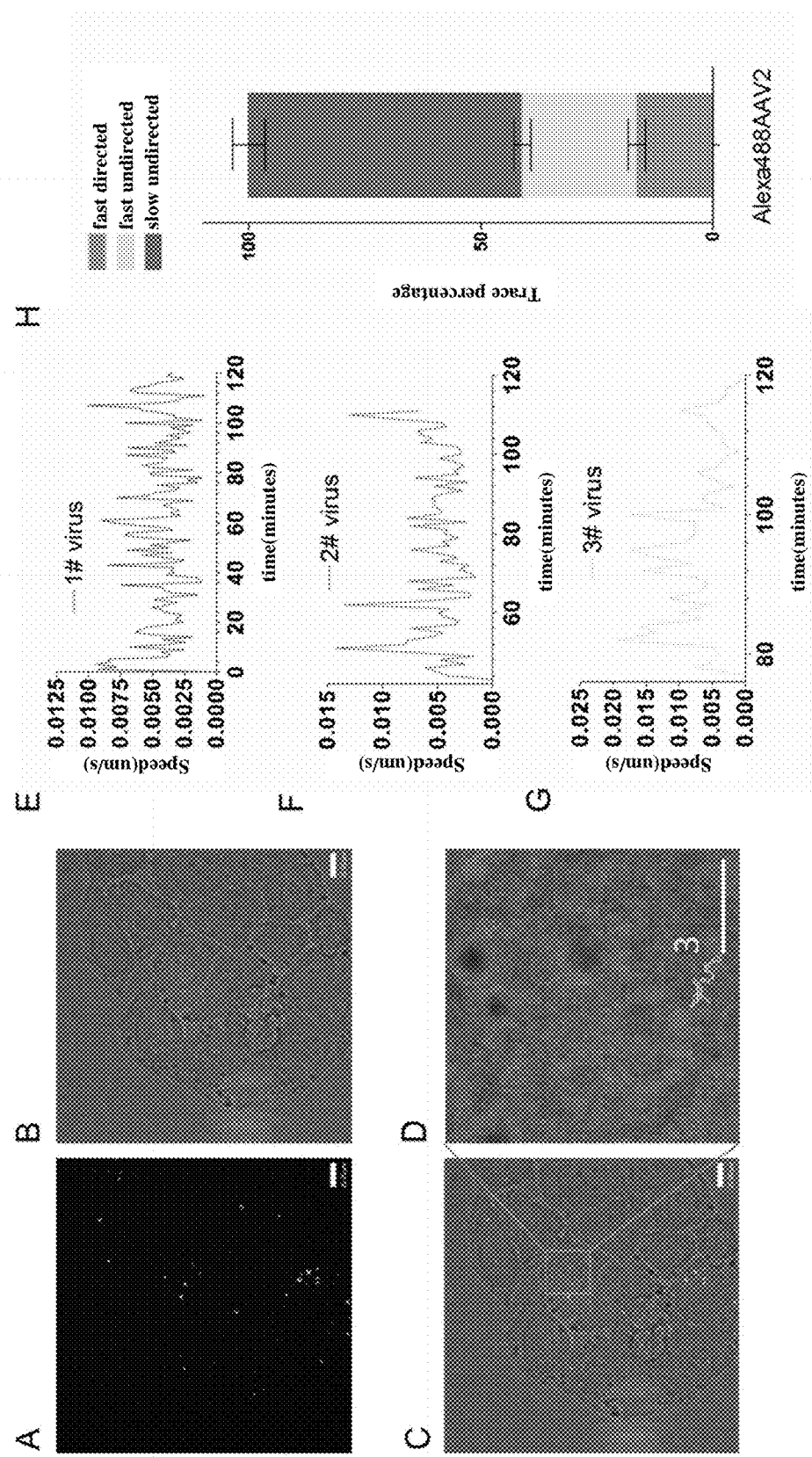

FIG. 9 shows quantitative analysis of viral movement of Alexa 488-tagged AAV2 in cells.

A, B and C show typical trace of movement of Alexa 488-tagged AAV2 in Hela cells; Hela cells are co-cultured with Alexa 488-tagged AAV2 at 4° C. for 30 min, then confocal real time imagery is recorded, in which A shows a fluorescence picture, B shows a white-light picture, C shows a picture of overlapped A and B, D shows an enlarged view of selected typical movements.

D shows typical movements of Alexa 488-tagged AAV2, in which 1 is fast and directed movement; 2 is fast and undirected movement; 3 is slow and undirected movement; and E, F, G show time trace of viral speeds.

H shows the trace of Alexa 488-AAV2 are classified as "slow undirected", "fast undirected", and "fast directed", in which "slow undirected" represents slow and undirected movement, "fast undirected" represents fast and undirected movement, "fast directed" represents fast and directed movement, error bar represents standard deviation of mean of 3 tests (195 trace in total), and proportional scale is equivalent to 10 μm.

Figure 10:
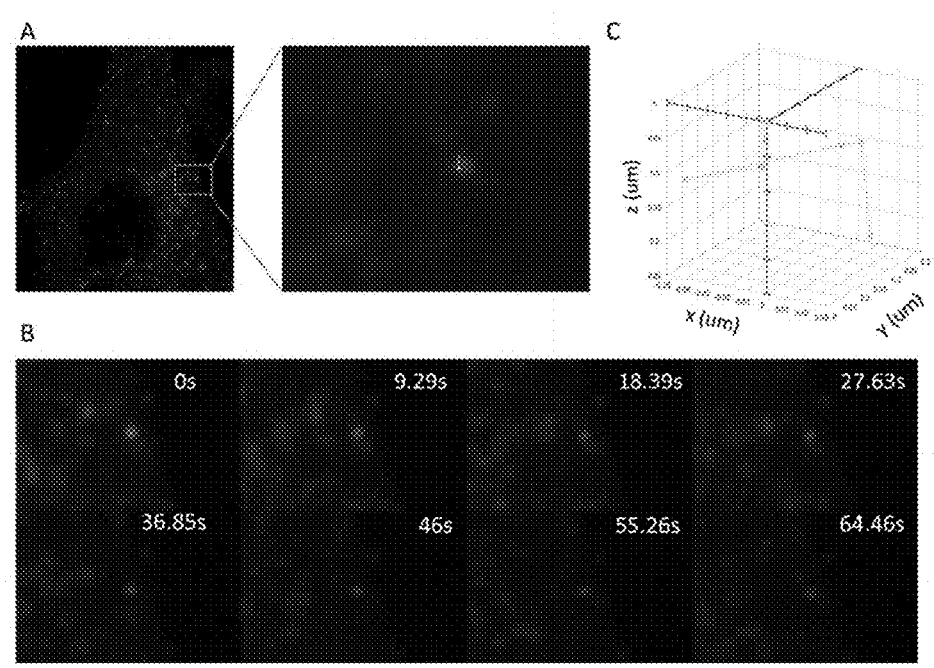

FIG. 10 shows a real-time monitored endocytosis process of Alexa488-AAV2 through clathrin coated pit.

After transfection for 24 h, cells and Alexa488-tagged AAV2 (green) are co-incubated at 4° C. for 30 min, then heated to 37° C. to start viral endocytosis, and confocal delayed imagery is recorded. It shows representative trace of Alexa488-AAV2 in Hela cells with expression of mRFP-clathrin (A), and selected read-time imaging frame (B). C shows three dimensional trace (green) of single AAV2 in Hela cells with expression of mRFP-clathrin.

Figure 11:
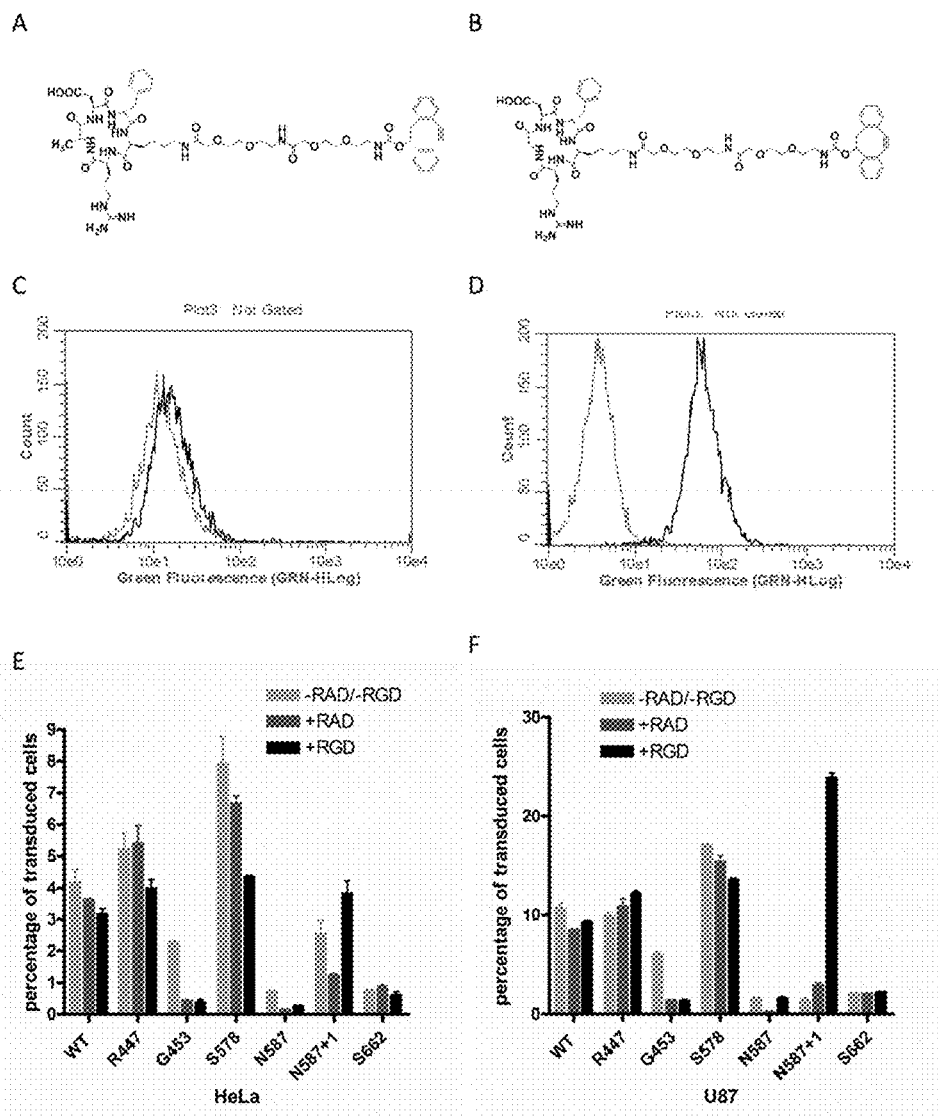

FIG. 11 shows gene transduction mediated by cRGD-modified AAV2-GFP vector;

A and B show chemical formulas of RAD-DIBO and RGD-DIBO;

C and D shows expression of integrin separately in Hela cells (left) and U87 cells (right) analyzed by flow cytometry techniques (FACS); expression of αvβ3 integrin is determined by antibody LM609; Alexa488-tagged anti-mouse antibody is used as second antibody for FACS detection (black line); hatchures are results of the negative control.

E and F show that cRGD-tagged vectors have higher gene transduction abilities separately to Hela cells and U87 cells; vectors without RAD/RGD labels and vectors with RAD/RGD labels in same amount are separately incubated with cells at 4° C. for 2 h; after removing unbound viruses, fresh culture media was added, and expression of GFP is analyzed after 48 h with FACS; the data represent percentage of transgenic cells with expression of eGFP, and the data are represented with mean and standard derivation of 3 repeated tests.

Figure 12:
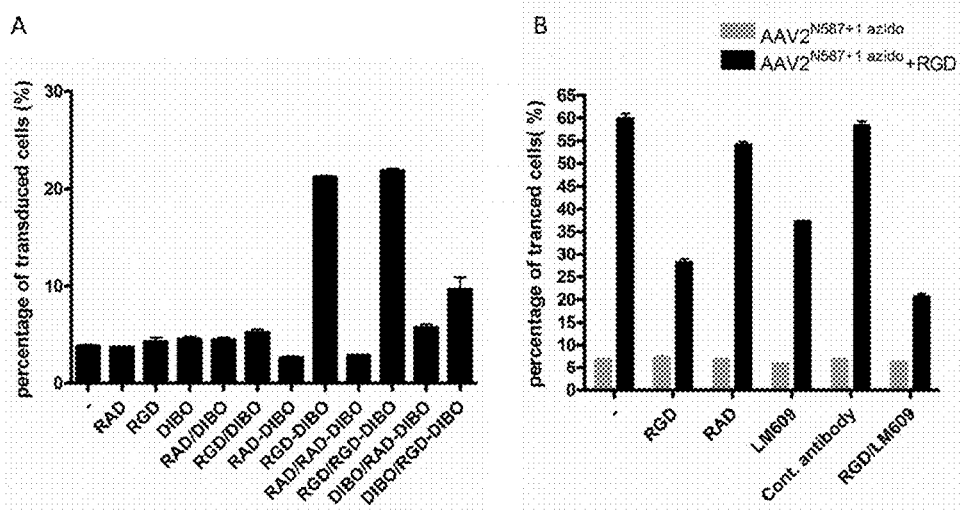

FIG. 12 show that RAD/RGD is successfully tagged on surface of AAV2-GFPcapsid protein via "click" reaction between NAEK and DIBO.

A shows that $AAV2^{N587+1/azido}$ (AAV2 is tagged with NAEK between N587 and R588) in dosage of 300 genome copies/cell are separately co-incubated with RAD, RGD, DIBO, RAD-DIBO, RGD-DIBO or a combination thereof at 4° C. for 2 h; redundant unreacted molecules are removed by using 100 kD Millipore Amicon Ultra-100; after dialysis, the viruses and U87 cells are incubated at 4° C. for 2 h; after unbound viruses are removed, fresh culture media is added, and GFP expression is analyzed by FACS after 48 h.

B shows competitive effects of integrin targeted transduction as mediated by $AAV2^{N587+1/aznido}$+RGD; U87 cells and $AAV2^{N587+1/azido}$+RGD (RGD-modified AAV2) or $AAV2^{N587+1/azido}$ (non-RGD-modified AAV2) are co-incubated at 4° C. for 2 h, in dosage of 700 genome copies/cell; after unbound viruses are removed, fresh culture media is added, and GFP expression is analyzed by FACS after 48 h; for the competitive tests, the binding between virus and cells is detected under conditions of 400 μg/ml RAD or RGD peptide, control or LM609 antibody (1:100 dilution), or combination of RGD peptide and LM609 antibody.

Figure 13:
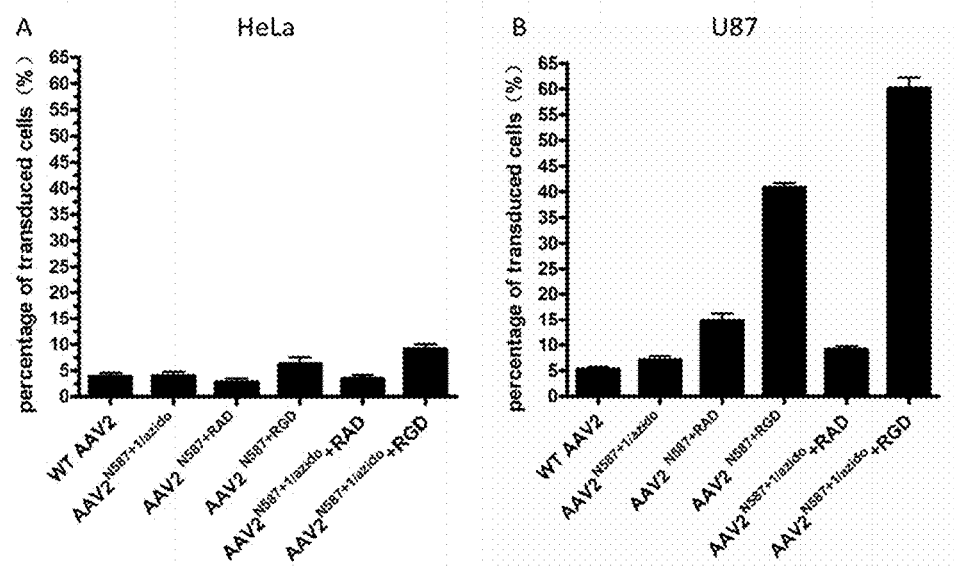

FIG. 13 show a comparison of transduction efficiencies of different viruses for Hela and U87 tumor cells;

WT AAV2 (wild-type AAV2), $AAV2^{N587+1/azido}$ (NAEK tag is inserted between sites 587 and 588 on surface of AAV2 capsid protein), $AAV2^{N587+RAD}$ (RAD peptide is inserted between sites 587 and 588 on surface of AAV2 capsid protein), $AAV2^{N587+RGD}$ (RGD peptide is inserted between sites 587 and 588 on surface of AAV2 capsid protein), AAV2$^{N587+1/azido}$+RAD (AAV2 is chemically linked to cRAD via NAEK and DIBO), and AAV2$^{N587+1/azido}$+RGD (AAV2 is chemically linked to cRGD via NAEK and DIBO) and Hela cells (A) or U87 cells (B) are incubated at 4° C. for 2 h, in dosage of 700 genome copies/cell; after unbound viruses are removed, fresh culture media is added, and GFP expression is analyzed by fluorescence microscope and FACS after 48 h; the results show that all viruses contain eGFP gene.

Figure 14:
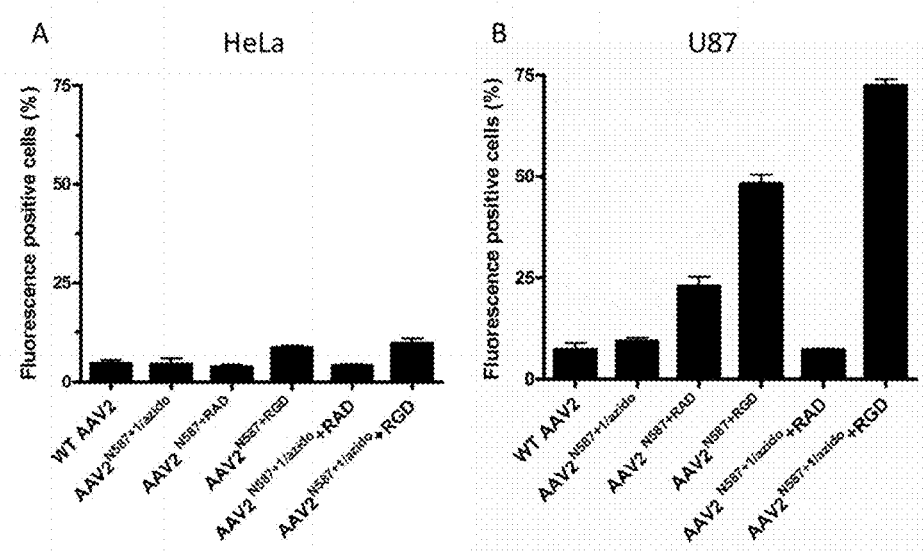

FIG. 14 shows binding force analysis of vector particles to Hela cells and U87 cells;

Virus vectors in same amount and cells are incubated at 4° C. for 2 h, then washed with PBS to remove unbound vector particles; the vector particles bound to Hela cells (A) or U87 cells (B) are detected by anti-AAV monoclonal antibody A20 and FACS.

Figure 15:
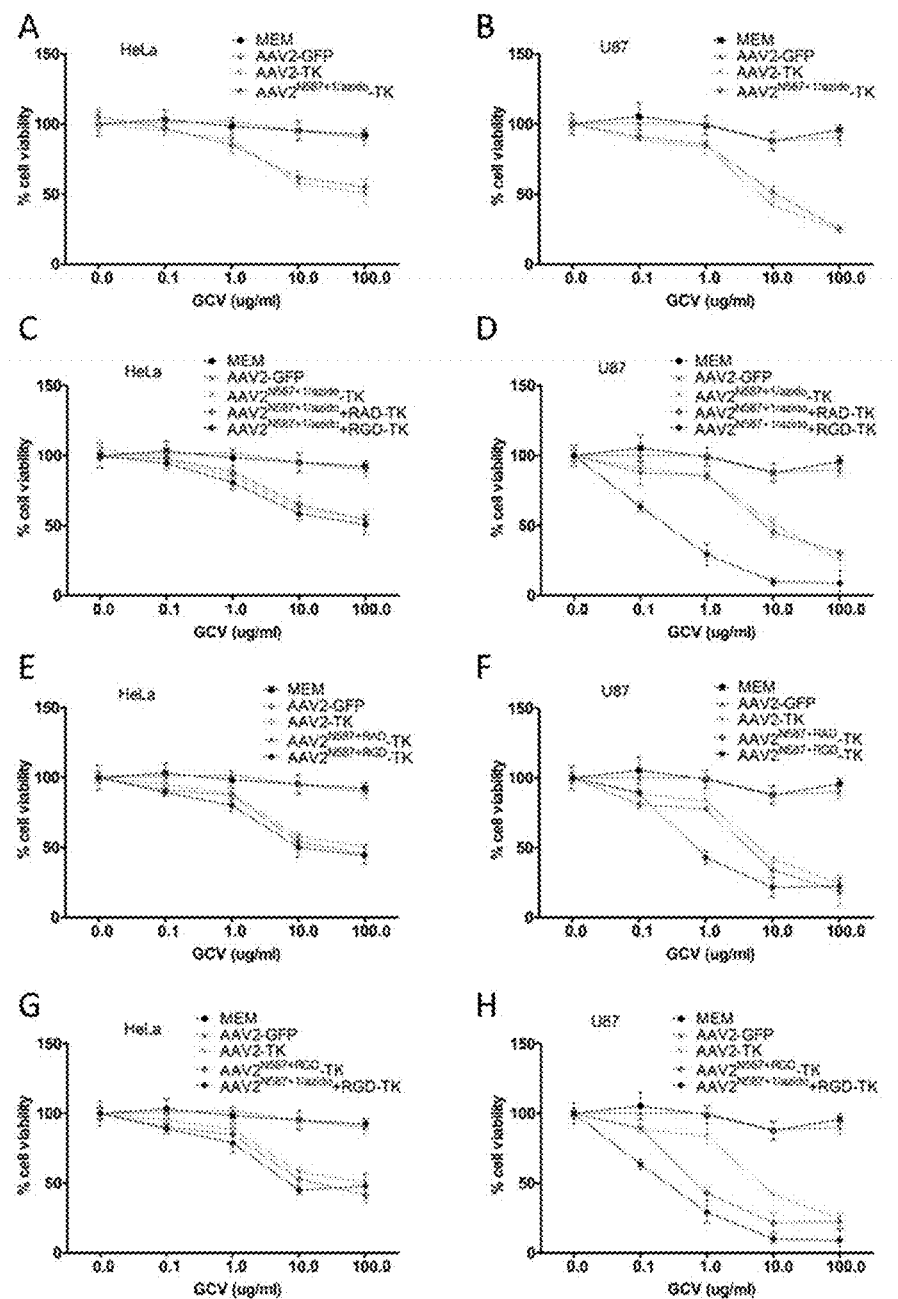

FIG. 15 show killing effects of AAV2-TK (thymidine kinase) with different modifications on Hela cells and U87 cells.

A, C, E and G show dose dependent cytotoxicity of Gancyclovir (GCV) on Hela/TK cells in vitro; AAV2-GFP (wild-type AAV2 containing GFP reporter gene), AAV2-TK (wild-type AAV2 containing thymidine kinase gene), and AAV2$^{N587+1/azido}$-TK (AAV2-TK integrated with NAEK at site N587+1), AAV2$^{N587+1/azido}$+RAD-TK (AAV2-TK is chemically coupled with cRAD via NAEK and DIBO), and AAV2$^{N587+1/azido}$+RGD-TK (AAV2-TK is chemically coupled with cRGD via NAEK and DIBO), AAV2$^{N587+RAD}$-TK (AAV2-TK is fused with RAD peptide between its capsid protein surface sites 587 and 588), AAV2$^{N587+RGD}$-TK (AAV2-TK is fused with RGD between its capsid protein surface sites 587 and 588) are incubated with U87 cells, in dosage of 500 genome copies/cell; these cells are incubated with GCV in different doses for 48 h, then cell survival rates are quantified by cell Titer-Glo (promega); MEM culture media is used as negative control.

B, D, F and G shows toxicity and dose-dependency of GCV on U87/TK cells in vitro; AAV2-GFP, AAV2-TK, and AAV2$^{N587+1/azido}$-TK, AAV2$^{N587+1/azido}$+RAD-TK, and AAV2$^{N587+1/azido}$+RGD-TK, AAV2$^{N587+RAD}$-TK, AAV2$^{N587+RGD}$-TK are incubated with U87 cells, in dosage of 500 genome copies/cell; these cells are incubated with GCV in different doses for 48 h, then cell survival rates are quantified by cell Titer-Glo (promega); MEM culture media is used as negative control.

Figure 16:
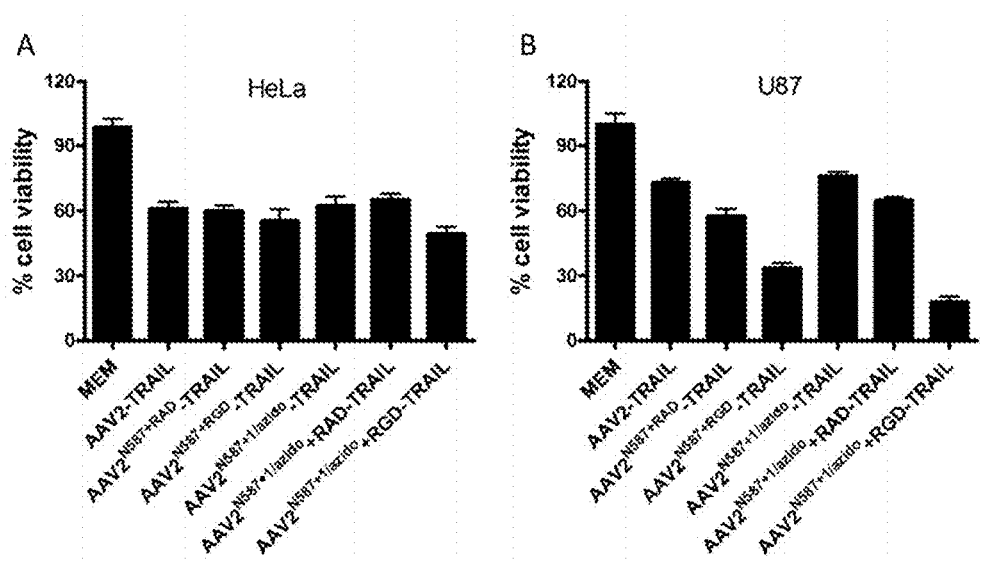

FIG. 16 shows killing effects of AAV2-TRAIL with different modifications on Hela cells and U87 cells;

Different AAV2 vectors containing TRAIL (TNF-related apoptosis-inducing ligand, tumor necrosis factor-related apoptosis-inducing ligand) gene are incubated with Hela cells (A) and U87 cells (B), in dosage of 500 genome copies/cell; after 48 h, cell survival rates are quantified by cell Titer-Glo (promega); MEM culture media is used as negative control.

Figure 17:
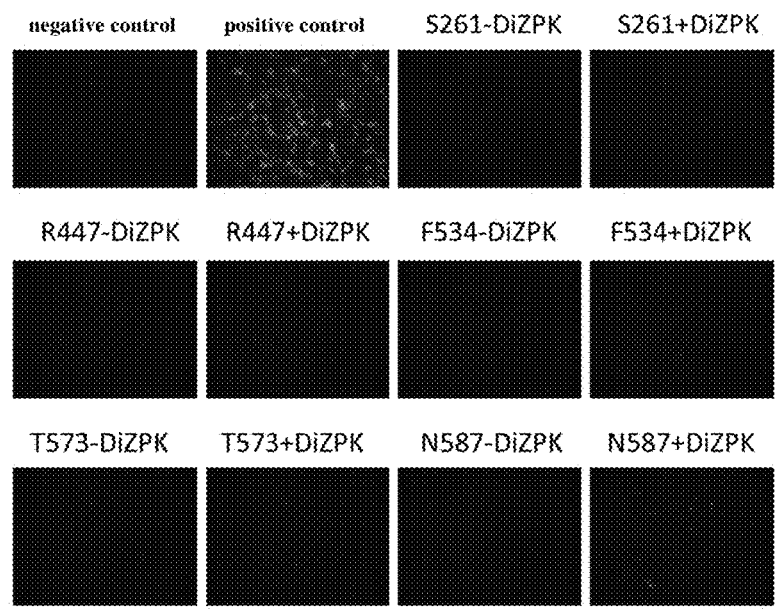

FIG. 17 shows imaging results of inserting DiZPK into different sites of AAV2 capsid.

SPECIFIC MODELS FOR CARRYING OUT THE INVENTION

The present invention is illustrated in details in conjunction with following examples, but those skilled in the art would understand these examples are used to illustrate the present invention only, rather than to limit the scope of the present invention. If specific conditions are not given in the examples, conventional conditions or conditions recommended by manufacturers are used. If reagents or instruments are not indicated with their manufacturers, they are all commercially available conventional products.

Experimental Materials and Methods
Cell Lines, Antibodies and Reagents

Culture media for AAV-293, HT-1080 and Hela cells are DMEM culture media (Zhongkemaichen Beijing Science and Technology Co., Ltd.) containing 10% fetal calf serum (PAA, Austria) and 2 mM L-glutamine (Zhongkemaichen Beijing Science and Technology Co., Ltd.), and cultured under condition of 5% $CO_2$. Anti-intact-AAV2 mouse monoclonal antibody (A20 clone) is obtained from ARP Company (American Research Products, Belmont, Mass.). DIBO-Alexa 488, DIBO-Alexa 555 stains are purchased from Invitrogen.

Synthesis of Nε-2-azidoethyloxycarbonyl-L-lysine (NAEK):

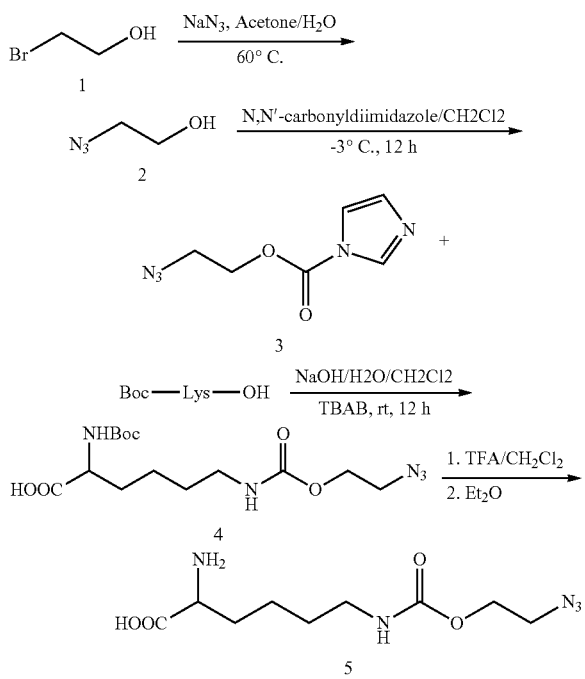

2-Bromoethanol (8 g, 64 mmol) and sodium azide (6.24 g, 96 mmol) were added at room temperature into acetone (60 ml) and water (30 ml). The reaction mixture solution was refluxed at 60° C. for 10 h, cooled to room temperature, vacuum evaporated to remove acetone. The residue was extracted with diethyl ether. The organic layer was washed with saline twice, then dried with $Na_2SO_4$, filtered, distilled, to obtain 2-azido-ethanol (Compound 2), yield 99% (5.5 g, 63.2 mmol), which is not further purified.

Compound 2 (5.5 g, 63.2 mmol) was dissolved in dichloromethane (120 ml), the resultant solution was slowly added at −3° C. into a suspension of N,N'-carbonyldiimidazole (15.36 g, 94.8 mmol) dissolved in dichloromethane (55 ml). The reaction was carried out under stirring condition for 12 h. Subsequently, 200 mL of water was added, the organic layer was washed with saline twice, then dried with $Na_2SO_4$, filtered and vacuum concentrated, the residue was further purified by silica gel chromatography, eluted with PE/EtOAc (1:1), to obtain Compound 3 in colorless oil form (10.7 g, 59 mmol), yield 93%.

Compound 3 (10.7 g, 59 mmol) was dissolved in dichloromethane (100 ml), the resultant solution is added at room temperature into Boc-Lys-OH (12.2 g, 49.2 mmol) in 1M NaOH aqueous solution (50 ml), then added with TBAB (0.16 g, 0.01 eq). The reaction mixture solution was stirred and reacted for 12 h, cooled to 0° C., then regulated with ice-bathed 1M HCl aqueous solution to have a pH value of 2-3. The water phase was extracted with DCM, and the organic layer was washed with saline twice. Subsequently, the organic layer was dried with $Na_2SO_4$, filtered and vacuum concentrated. The residue was purified by silica gel chromatography, eluted with PE/EtOAc/HAc (100:100:1), to obtain Compound 4 in colorless oil form (15.1 g, 41.94 mmol), yield 85%.

Compound 4 (15.1 g, 41.94 mmol) was dissolved in dichloromethane (80 ml), then slowly added with trifluoroacetic acid (20 ml). The reaction solution was stirred and reacted at room temperature for 0.5 h, then vacuum evaporated to remove solvent. The residue was re-dissolved in methanol (5 ml), and precipitated in ethyl ether. The precipitate was collected and vacuum dried to obtain Compound 5 in white solid form (6.63 g, 25.58 mmol), i.e., NAEK, yield 61%.

Synthesis and Identification of Non-Natural Amino Acid DiZPK:

The reaction scheme for chemical synthesis of non-natural amino acid DiZPK is as follows:

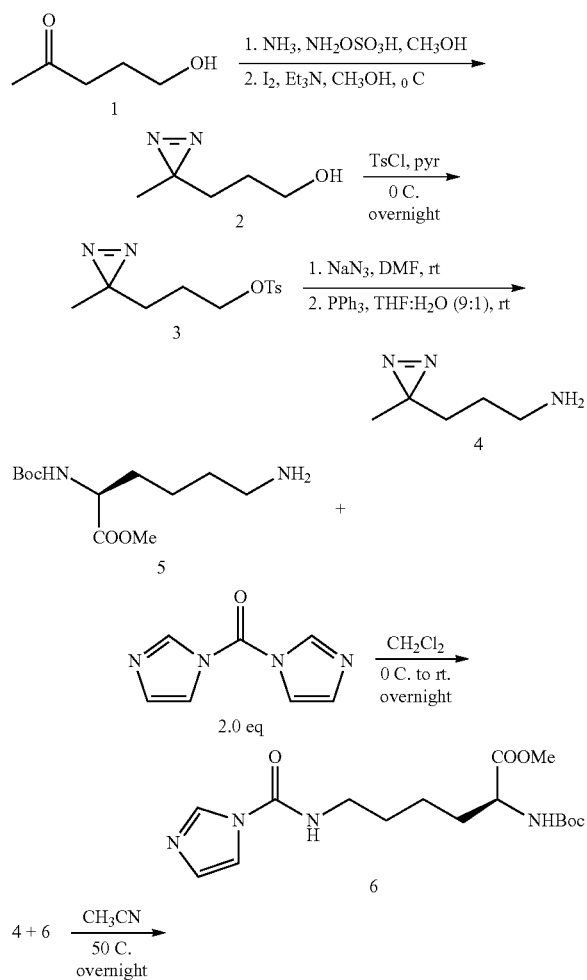

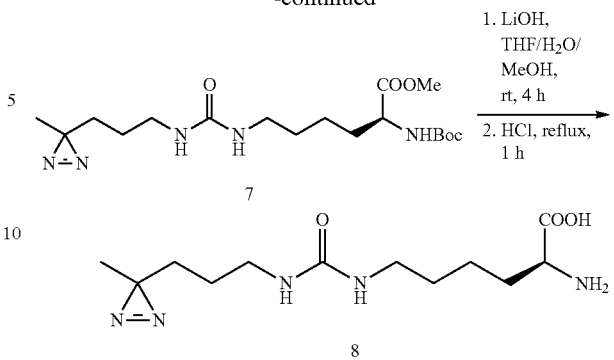

As shown in the scheme, 15 mL of raw material 1 (5-hydroxy-2-pentanone) and 40 mL of liquid ammonia were stirred and reacted at −40° C. for 5 h, then cooled to −60° C., slowly added dropwise with $NH_2OSO_3H$ (20 g) in methanol solution, after addition, heated to room temperature, reacted overnight, filtered to remove precipitate. The supernatant was added with triethylamine, slowly added with $I_2$ under ice-bath condition, until the reaction solution became dark and did nog generate bubbles. After the end of reaction, the solvent was removed by distillation, the product was extracted with ethyl ether and then dried. After ethyl ether ws removed by distillation, the residual liquid was evaporated under reduced pressure to obtain 25.4 g of Product 2 in colorless viscous liquid form.

The Product 2 was dissolved in pyridine, added at 0° C. under stirring with 11 g of TsCl, reacted overnight. After the end of reaction, the reaction solution was poured into a mixture solution of concentrated hydrochloride acid and ice-water, extracted with ethyl ether, the ether layer was washed with 1N hydrochloric acid and 1N NaOH separately. The organic phase was separated by a drying column to obtain 11.8 g of Product 3 in colorless viscous liquid form.

The above Product 3 was dissolved in DMF, added with $NaN_3$ and reacted at room temperature overnight. After the end of reaction, a large amount of water was added, extracted with ethyl ether. After removal of ethyl ether by distillation, the residual product was dissolved in THF:water (9:1), added with triphenyl phosphine, reacted at room temperature. After the end of reaction, 1N HCl was added and mixed homogeneously, then THF was rotationally dried, unreacted raw materials, PPh3 and O=PPh3 were washed off with dichloromethane, the liquid phase was added with 1N NaOH to regulate pH at 12, extracted with dichloromethane to obtain 4.0 g of Product 4.

5.2 g of raw material 5 (Boc-Lys-OMe) reacted with carbonyldiimidazole to prepare 5.9 g of Compound 6. Subsequently, Compound 6 was coupled to Product 4 (4.0 g) to obtain Compound 7, which was finally subjected to two-step deprotection to remove Boc and methyl ester, so as to obtain 4.5 g of Product 8, i.e., DiZPK. Results of spectroscopy are as follows:

$^1$H NMR (400 MHz, $D_2O$): δ 3.10 (1H, t, J=6.3 Hz), 2.96 (4H, m), 1.25 (10H, m), 0.90 (3H, s); $^{13}$C NMR (100 MHz, $D_2O$): 183.63, 160.66, 56.00, 39.80, 39.30, 34.49, 30.84, 29.20, 26.75, 23.92, 22.43, 18.80; HREIMS m/z 308.16937 [M+1]$^+$ (calcd for $C_{12}H_{22}N_5NaO_3$, 308.16931), which confirm that the obtained DiZPK has correct structure.

Culture of Incasing Cells

AAV-293 cells (Stratagene) were used to produce recombination infective AAV particles. In the present invention, only AAV2 serotype was prepared and used. AAV-293 cells represented human fetal renal cells with stably transfected type 5 adenovirus DNA, and had adenovirus e1 gene for in vitro preparation of rAAV. In order to prepare rAAV, ADENO-ASSOCIATED VIRUS-293 cells were cultured in DMEM culture media, and added with 10% fetal calf serum, 4 mM L-glutamine and 4.5 g/L glucose, the culture conditions were 37° C., 5% $CO_2$. After the cells were cultured to spread 60-70% area, triple co-transfection of AAV plasmid started.

Plasmid Construction

Expression plasmid vectors pAAV-RC, pHelper and pAAV-GFP (Agilent, Santa Clara, Calif.) were used in the experiment. The construct contained AAV and adenovirus genes for preparing infectious AAV particles. The pAAV-RC provided rep gene and cap gene separately for encoding AAV replication and capsid protein. The pHelper vector contained adenovirus E2A, E4 and VA genes, and the pAAV-GFP contained GFP reporter gene. This reporter vector represents ITR-containing plasmid, and the plasmid had cmv promoter. The pAAV-RC-R447 plasmid was prepared by using Quik Change Lightning Site-Directed Mutagenesis Kit (Agilent), in which the genetic code of arginine residue at site 447 of AAV capsid protein VP1 is mutated as TAG. Other mutant plasmids were constructed by same methods.

The pACYC-tRNA/Py1RS containing a gene encoding orthogonal amber mutant suppressor aminoacyl-tRNA synthase/$tRNA_{CUA}$ was a gift of Professor CHEN Peng of College of Chemistry of Peking University (Duy P. Nguyen, Hrvoje Lusic, Heinz Neumann, Prashant B. Kapadnis, Alexander Deiters, and Jason W. Chin. Genetic Encoding and Labeling of Aliphatic Azides and Alkynes in Recombinant Proteins via a Pyrrolysyl-tRNA Synthetase/$tRNA_{CUA}$Pair and Click Chemistry. J. AM. CHEM. SOC. 2009, 131, 8720-8721).

The plasmid pACYC-tRNA/Py1RS was obtained from *Escherichia coli* pACYC-tRNA/Py1RS (a gift of Professor CHEN Peng of College of Chemistry of Peking University), which contained plasmid pACYC-tRNA/Py1RS and named as *Escherichia coli*, and deposited in China General Microbiological Culture Collection Center (Address: NO. 1 West Beichen Road, Chaoyang District, Beijing 100101, Institute of Microbiology, Chinese Academy of Sciences) on Jun. 14, 2011 with a deposition number of CGMCC No: 4951. The plasmid could be used to express tRNA and tRNA synthase for specifically identifying non-natural amino acids DiZPK and NAEK, the deposition information thereof had been disclosed in the patent application with publication number of CN102838663A.

Preparation and Purification of AAV

In AAV Helper-Free System, azido-tagged AAV2 infectious particles (e.g., R447-AAV2 vector) was prepared, and assistant adenovirus or herpes virus were not used in infection. AAV2 plasmid vector pAAV-RC, pHelper, pAAV-GFP and vector pACYC-tRNA/Py1RS (molar ratio=1:1:1:2) were used for transient co-transfection of AAV-293 incasing cells by calcium phosphate precipitation method. After 6 h of transfection, the cell culture media was replaced with a fresh culture media containing 1 mM NAEK. After 72 h, infected cells were collected. In order to release rAAV virus particles, the infected cells were lysed by freeze-thaw method. Separation and purification processes were carried out by referring to the operations of Ping Guo, et al (Guo P, El-Gohary Y, Prasadan K, Shiota C, Xiao X, Wiersch J, Paredes J, Tulachan S, Gittes G K: Rapid and simplified purification of recombinant adeno-associated virus. *J Virol Methods*, 183(2):139-146).

Determination of Viral Titer

AAV-HT1080 cells were cultured in 6-well tissue culture plate, each well had 2 ml of DMEM culture media, and cell density was $3 \times 10^5$/well. Culture was carried out at 37° C. overnight. The cells were culture to spread about 50% area. Virus storing solution was diluted by 10 times. On the basis of 10 times dilution, dilution by 5 times was performed in volume of 5 ml, and concentrations ranged from $2 \times 10^{-2}$ to $8 \times 10^{-4}$. The diluted solutions in volume of 1 ml were added into wells of the 6-well plate, 3 wells for each titer. In the meantime, the well without adding virus storing solution was used as negative control. Incubation was performed at 37° C. for 1-2 h. During incubation, the culture plate was gently vortex shaken at intervals of 30 min. Subsequently, each well was added with 1 ml of pre-heated H-DMEM and cultured at 37° C. for 40-48 h. The pAAV-hrGFP AAV infected cells were detected by FACS.

Quantification of Genome Copies by Using Real-time Quantitative PCR (qPCR)

The genome copies of vectors were quantified by using Mx3000P real-time PCR meter (Agilent Technologies, La Jolla, Calif., USA), in which the GFP gene-specific primer pair was: 5'-AAGCAGCACGACTTCTTCAAGTC-3' (SEQ ID NO: 31) (forward) and 5'-TCGCCCTCGAACTTCAC-CTC-3' (SEQ ID NO: 32) (reverse). The detail of method can be seen in the published operation guide[20].

Fluorescence Probe Ligation

For fluorescence labeling of AAV2-azido, the purified virus particles were incubated with Alexa488-DIBO or Alexa 555 (500 μM) at room temperature at pH7.0 for 2 h. 100 kD Millipore Amicon Ultra-100 was used to remove unreacted stains.

The method for linking targeting molecule cRGD was similar to that for fluorescence probe ligation.

Confocal Imaging

Alexa488-tagged AAV2 and Hela cells were co-cultured in a glass bottom culture dish at 37° C. for 30 min, then the cells were fixed with phosphate buffer solution (pH 7.0) (PBS) containing 4% paraformaldehyde for 15 min. Subsequently, the cells were permeabilized in PBS solution containing 0.5% Triton X-100 for 10 min, and sealed with PBS containing 3% bovine serum albumin (BSA) for 60 min. Subsequently, the cells were incubated with anti-intact AAV2 mouse monoclonal antibody (A20) at 4° C. overnight, and then incubated at room temperature for 1 h with a second antibody (life technology) that links to Alexa594. The cell nucleus were stained with DAPI (Sigma). Imagery was performed by confocal laser-scanning microscopy (SP8 Series, Leica, Germany).

Imagery of Living Cells

In order to real-time observe movement of Alexa488-AAV2, Hela cells were inoculated in glass bottom culture dish, cultured at 37° C. overnight. Subsequently, Alexa488-tagged AAV2 and Hela cells were co-cultured at 4° C. for 30 min, and then confocal real-time imagery was recorded by using a living cell imaging system (PerkinElmer, MA, USA).

EXAMPLE 1

Mutation Site Selection and Mutant Primer Design for Adeno-associated Virus Capsid Protein (1) Selection of Mutation Sites In the adeno-associated virus capsid protein VP1, the mutation sites as shown in Table 1 were selected, wherein the amino acid sequence of VP1 protein was as follows:

(SEQ ID NO: 1)
MAADGYLPDWLEDTLSEGIRQWWKLKPGPPPPKPAERHKDDSRGLVLPGY
KYLGPFNGLDKGEPVNEADAAALEHDKAYDRQLDSGDNPYLKYNHADAEF
QERLKEDTSFGGNLGRAVFQAKKRVLEPLGLVEEPVKTAPGKKRPVEHSP
VEPDSSSGTGKAGQQPARKRLNFGQTGDADSVPDPQPLGQPPAAPSGLGT
NTMATGSGAPMADNNEGADGVGNSSGNWHCDSTWMGDRVITTSTRTWALP
TYNNHLYKQISSQSGASNDNHYFGYSTPWGYFDFNRFHCHFSPRDWQRLI
NNNWGFRPKRLNFKLFNIQVKEVTQNDGTTTIANNLTSTVQVFTDSEYQL
PYVLGSAHQGCLPPFPADVFMVPQYGYLTLNNGSQAVGRSSFYCLEYFPS
QMLRTGNNFTFSYTFEDVPFHSSYAHSQSLDRLMNPLIDQYLYYLSRTNT
PSGTTTQSRLQFSQAGASDIRDQSRNWLPGPCYRQQRVSKTSADNNNSEY
SWTGATKYHLNGRDSLVNPGPAMASHKDDEEKFFPQSGVLIFGKQGSEKT
NVDIEKVMITDEEEIRTTNPVATEQYGSVSTNLQRGNRQAATADVNTQGV
LPGMVWQDRDVYLQGPIWAKIPHTDGHFHPSPLMGGFGLKHPPPQILIKN
TPVPANPSTTFSAAKFASFITQYSTGQVSVEIEWELQKENSKRWNPEIQY
TSNYNKSVNVDFTVDTNGVYSEPRPIGTRYLTRNL;

the nucleotide sequence for VP1 protein was as follows:

(SEQ ID NO: 2)
ATGGCTGCCGATGGTTATCTTCCAGATTGGCTCGAGGACACTCTCTCTGA
AGGAATAAGACAGTGGTGGAAGCTCAAACCTGGCCCACCACCACCAAAGC
CCGCAGAGCGGCATAAGGACGACAGCAGGGGTCTTGTGCTTCCTGGGTAC
AAGTACCTCGGACCCTTCAACGGACTCGACAAGGGAGAGCCGGTCAACGA
GGCAGACGCCGCGGCCCTCGAGCACGACAAAGCCTACGACCGGCAGCTCG
ACAGCGGAGACAACCCGTACCTCAAGTACAACCACGCCGACGCGGAGTTT
CAGGAGCGCCTTAAAGAAGATACGTCTTTTGGGGGCAACCTCGGACGAGC
AGTCTTCCAGGCGAAAAAGAGGGTTCTTGAACCTCTGGGCCTGGTTGAGG
AACCTGTTAAGACGGCTCCGGGAAAAAAGAGGCCGGTAGAGCACTCTCCT
GTGGAGCCAGACTCCTCCTCGGGAACCGGAAAGGCGGGCCAGCAGCCTGC
AAGAAAAAGATTGAATTTTGGTCAGACTGGAGACGCAGACTCAGTACCTG
ACCCCCAGCCTCTCGGACAGCCACCAGCAGCCCCCTCTGGTCTGGGAACT
AATACGATGGCTACAGGCAGTGGCGCACCAATGGCAGACAATAACGAGGG
CGCCGACGGAGTGGGTAATTCCTCGGGAAATTGGCATTGCGATTCCACAT
GGATGGGCGACAGAGTCATCACCACCAGCACCCGAACCTGGGCCCTGCCC
ACCTACAACAACCACCTCTACAAACAAATTTCCAGCCAATCAGGAGCCTC
GAACGACAATCACTACTTTGGCTACAGCACCCCTTGGGGGTATTTTGACT
TCAACAGATTCCACTGCCACTTTTCACCACGTGACTGGCAAAGACTCATC
AACAACAACTGGGGATTCCGACCCAAGAGACTCAACTTCAAGCTCTTTAA
CATTCAAGTCAAAGAGGTCACGCAGAATGACGGTACGACGACGATTGCCA
ATAACCTTACCAGCACGGTTCAGGTGTTTACTGACTCGGAGTACCAGCTC
CCGTACGTCCTCGGCTCGGCGCATCAAGGATGCCTCCCGCCGTTCCCAGC
AGACGTCTTCATGGTGCCACAGTATGGATACCTCACCCTGAACAACGGGA
GTCAGGCAGTAGGACGCTCTTCATTTTACTGCCTGGAGTACTTTCCTTCT
CAGATGCTGCGTACCGGAAACAACTTTACCTTCAGCTACACTTTTGAGGA
CGTTCCTTTCCACAGCAGCTACGCTCACAGCCAGAGTCTGGACCGTCTCA
TGAATCCTCTCATCGACCAGTACCTGTATTACTTGAGCAGAACAAACACT
CCAAGTGGAACCACCACGCAGTCAAGGCTTCAGTTTTCTCAGGCCGGAGC
GAGTGACATTCGGGACCAGTCTAGGAACTGGCTTCCTGGACCCTGTTACC
GCCAGCAGCGAGTATCAAAGACATCTGCGGATAACAACAACAGTGAATAC
TCGTGGACTGGAGCTACCAAGTACCACCTCAATGGCAGAGACTCTCTGGT
GAATCCGGGCCCGGCCATGGCAAGCCACAAGGACGATGAAGAAAAGTTTT
TTCCTCAGAGCGGGGTTCTCATCTTTGGGAAGCAAGGCTCAGAGAAAACA
AATGTGGACATTGAAAAGGTCATGATTACAGACGAAGAGGAAATCAGGAC
AACCAATCCCGTGGCTACGGAGCAGTATGGTTCTGTATCTACCAACCTCC
AGAGAGGCAACAGACAAGCAGCTACCGCAGATGTCAACACACAAGGCGTT
CTTCCAGGCATGGTCTGGCAGGACAGAGATGTGTACCTTCAGGGGCCCAT
CTGGGCAAAGATTCCACACACGGACGGACATTTTCACCCCTCTCCCCTCA
TGGGTGGATTCGGACTTAAACACCCTCCTCCACAGATTCTCATCAAGAAC
ACCCCGGTACCTGCGAATCCTTCGACCACCTTCAGTGCGGCAAAGTTTGC
TTCCTTCATCACACAGTACTCCACGGGACAGGTCAGCGTGGAGATCGAGT
GGGAGCTGCAGAAGGAAAACAGCAAACGCTGGAATCCCGAAATTCAGTAC
ACTTCCAACTACAACAAGTCTGTTAATGTGGACTTTACTGTGGACACTAA
TGGCGTGTATTCAGAGCCTCGCCCCATTGGCACCAGATACCTGACTCGTA
ATCTGTAA.

TABLE 1

| Mutation sites | | | |
|---|---|---|---|
| Amino acid site | Amino acid | Codon before mutation | Codon after mutation |
| 261 | S | TCC | TAG |
| 381 | N | AAC | |
| 444 | Y | TAC | |
| 447 | R | AGA | |
| 453 | G | GGA | |
| 458 | S | TCA | |
| 492 | S | TCT | |
| 500 | Y | TAC | |
| 534 | F | TTT | |
| 573 | T | ACG | |
| 578 | S | TCT | |
| 587 | N | AAC | |
| 662 | S | AGT | |

The sites in Table 1 are sites in VP1 protein.

(2) Design of Mutant Primers

In order to site-specifically mutate the sites in Table 1, the mutant primers in Table 2 were designed (which could be also used as sequencing primers).

TABLE 2

List of mutant primers

| SEQ ID NO | Mutation site | Primer direction | Primer sequence |
|---|---|---|---|
| 3 | VP1Y444 | #1 | CTCATCGACCAGTACCTGTATTAGTTGAGCAGAACAAACAC |
| 4 | VP1Y444 | #2 | GTGTTTGTTCTGCTCAACTAATACAGGTACTGGTCGATGAG |
| 5 | VP1G453 | #1 | GCAGAACAAACACTCCAAGTTAGACCACCACGCAGTCAAGGC |
| 6 | VP1G453 | #2 | GCCTTGACTGCGTGGTGGTCTAACTTGGAGTGTTTGTTCTGC |
| 7 | VP1S458 | #1 | CAAGTGGAACCACCACGCAGTAGAGGCTTCAGTTTTCTC |
| 8 | VP1S458 | #2 | GAGAAAACTGAAGCCTCTACTGCGTGGTGGTTCCACTTG |
| 9 | VP1S492 | #1 | CAGCAGCGAGTATCAAAGACATAGGCGGATAACAACAACAGTG |
| 10 | VP1S492 | #2 | CACTGTTGTTGTTATCCGCCTATGTCTTTGATACTCGCTGCTG |
| 11 | VP1Y500 | #1 | GGATAACAACAACAGTGAATAGTCGTGGACTGGAGCTACC |
| 12 | VP1Y500 | #2 | GGTAGCTCCAGTCCACGACTATTCACTGTTGTTGTTATCC |
| 13 | VP1 S578 | #1 | GGCTACGGAGCAGTATGGTTAGGTATCTACCAACCTCC |
| 14 | VP1 S578 | #2 | GGAGGTTGGTAGATACCTAACCATACTGCTCCGTAGCC |
| 15 | VP1N587 + 1 | #1 | CCAACCTCCAGAGAGGCAACTAGAGACAAGCAGCTACCGC |
| 16 | VP1N587 + 1 | #2 | GCGGTAGCTGCTTGTCTCTAGTTGCCTCTCTGGAGGTTGG |
| 17 | VP1 S662 | #1 | CGAATCCTTCGACCACCTTCTAGGCGGCAAAGTTTGCTTCC |
| 18 | VP1 S662 | #2 | GGAAGCAAACTTTGCCGCCTAGAAGGTGGTCGAAGGATTCG |
| 19 | VP1 S261 | #1 | CACCTCTACAAACAAATTTAGAGCCAATCAGGAGCCTCGAAC |
| 20 | VP1 S261 | #2 | GTTCGAGGCTCCTGATTGGCTCTAAATTTGTTTGTAGAGGTG |
| 21 | VP1 N381 | #1 | CAGTATGGATACCTCACCCTGTAGAACGGGAGTCAGGCAG |
| 22 | VP1 N381 | #2 | CTGCCTGACTCCCGTTCTACAGGGTGAGGTATCCATACTG |
| 23 | VP1 R447 | #1 | CAGTACCTGTATTACTTGAGCTAGACAAACACTCCAAGTGGAACC |
| 24 | VP1 R447 | #2 | GGTTCCACTTGGAGTGTTTGTCTAGCTCAAGTAATACAGGTACTG |
| 25 | VP1 F534 | #1 | GGACGATGAAGAAAAGTTTTAGCCTCAGAGCGGGGTTCTCATC |
| 26 | VP1 F534 | #2 | GATGAGAACCCCGCTCTGAGGCTAAAACTTTTCTTCATCGTCC |
| 27 | VP1 T573 | #1 | GGACAACCAATCCCGTGGCTTAGGAGCAGTATGGTTCTG |
| 28 | VP1 T573 | #2 | CAGAACCATACTGCTCCTAAGCCACGGGATTGGTTGTCC |
| 29 | VP1 N587 | #1 | CTACCAACCTCCAGAGAGGCTAGAGACAAGCAGCTACC |
| 30 | VP1 N587 | #2 | GGTAGCTGCTTGTCTCTAGCCTCTCTGGAGGTTGGTAG |

In Table 2, #1 represents forward primer, #2 represents reverse primer; 587 + 1 represents an non-natural amino acid was inserted after site 587, i.e., the non-natural amino acid was inserted between site 587 and site 588.

EXAMPLE 2

Expression and Detection of Adeno-associated Virus VP1 Mutant Protein

Firstly, we observed the compatibility of orthogonal amber mutant suppresser aminoacyl-tRNA synthase/tRNA$_{CUA}$ system in AAVcapsid protein VP1 expression. VP1 gene was cloned into vector pCMV-FLAG (FLAG tag at C-terminal), to obtain VP1 coding vector pCMV-VP1-FLAG. By using Quik Change Lightning Site-Directed Mutagenesis Kit (Agilent) according to its instruction, the codons in the vector that encode residues S261, N381, Y444, R447, G453, S458, S492, Y500, F534, T573, S578, N587, N587+1, S662 were mutated as amber termination codon (TAG) by using pCMV-VP1-FLAG plasmid as template and using the mutant primers as listed in Table 2. The sequencing results show that these mutations had been successfully introduced. The plasmid obtained by mutation at site R447 was named as pCMV-VP1-FLAG-R447, which represented that the genetic codon of arginine residue at site 447 of AAVcapsid protein VP1 was mutated as TAG, and other plasmids obtained after mutation were named according to the same principle.

Subsequently, it was verified whether the mutant plasmid could correctly exhibit NAEK in 293T cells via co-expression of NAEK-specific orthogonal tRNA/aaRS vector. The results of Western blotting showed that when the 293T cells were cultured in a culture media containing NAEK, all mutant VP1 proteins could be detected by using anti-FLAG antibody; the expression levels of mutant VP1 were about 10-100% that of wild-type protein upon different mutation sites (FIG. 2A, 2B). If the 293T cells were cultured under conditions without NAEK, VP1 proteins could be detected. Further, NAEK was inserted at site G453 of VP1 and the exhibition of NAEK was confirmed by MS/MS sequencing (FIG. 2D).

In addition, the orthogonal reactions with DIBO-Alexa488 (a fluorescence tag of single virus) under moderate conditions also confirmed that NAEK was inserted in VP1 protein (FIG. 2C), and bright green fluorescence was observed when mutant VP1 protein and fluorescence group were co-incubated at 4° C. for 1 h. With regard to wild-type VP1 protein or mutant VP1 proteins without being treated with fluorescence group, green signal was not observed (FIG. 2C). The experimental results indicated that NAEK was successfully tagged on VP1 protein, and other molecules could be further coupled via NAEK.

EXAMPLE 3

Site-specifically Mutated Adeno-associated Virus and Detection Thereof

In the present invention, genetic code expanding techniques were used to site-specifically tag AAV2 by introducing azido-containing amino acid NAEK into virus capsid.

By using Quik Change Lightning Site-Directed Mutagenesis Kit (Agilent) according to its instruction, mutations were fulfilled by using pAAV-RC plasmid as template and using the mutant primers as listed in Table 2. The sequencing results showed that these mutations were successfully introduced. The plasmid obtained by mutation at site R447 was named as pAAV-RC-R447, which represented that the genetic codon of arginine residue at site 447 of AAV capsid protein VP1 was mutated as TAG, and other plasmids obtained after mutation were named according to the same principle.

As shown in FIG. 3A, the present invention used genetic methods to insert azido-containing non-natural amino acid at amino acid site 447 of VP1/VP2/VP3 zones where cap gene was located. Correspondingly, the genetic codon of AAV2 capsid protein encoding plasmid pAAV-RC was mutated, i.e., mutated as amber terminal codon TAG. Subsequently, in the presence of NAEK, mutant plasmid pAAV-RC-R447 was used for passage of azido-containing AAV2 (R447-AAV2) particles by co-expression of NAEK specific orthogonal tRNA/aaRS pair (pACYC-tRNA/Py1RS vector), pHelper vector and pAAV-GFP vector in AAV-293 incasing cells (see details in section of "Materials and Methods"). After 72 h, cell lysate was collected, diluted by 10 times and added to HT-1080 cells, and fluorescence microscopy was used to detect whether mutant viruses were produced.

The NAEK-containing cell lysate obtained after mutant plasmid transfection was used to transfect HT-1080 cells, and we found very strong green fluorescence in HT-1080 cells after HT-1080 cells were transfected for 48 h, which was almost equivalent to that of wild-type, but shoed no significant difference from NAEK (see FIG. 3B, 3C).

Specific experimental methods could be seen in "Preparation and purification of AAV" in section of materials and methods.

NAEK could be inserted at sites G453, S578, N587, N587+1, S662, besides site R447 (see FIG. 4, FIG. 6A, FIG. 6B). However, sites S261, N381, Y444, S458, S492, Y500, F534, T573 could not be tagged with NAEK (see FIG. 5, FIG. 6C, FIG. 6D). The specific experimental method were the same as above.

This indicated that due to the presence of NAEK, it was successful to use mutant AAV2 capsid to package ADENO-ASSOCIATED VIRUS. In addition, both of modified or untagged AAV2 carrying GFP reporter gene were used to infect HT-1080 cells, and to detect viral titer, and qPCR was used to detect viral genome titer. The functional titer values of R447-AAV2 and S578-AAV2 (transfection unit/ml) were equivalent to that of WT-AAV2 (see: FIG. 6E, FIG. 6F), which showed that introducing azido tag had very small influence on production and transfection ability of AAV2 particles.

EXAMPLE 4

Fluorescence Modification of AAV2 Site-specifically Labeled with NAEK

Figure 1:
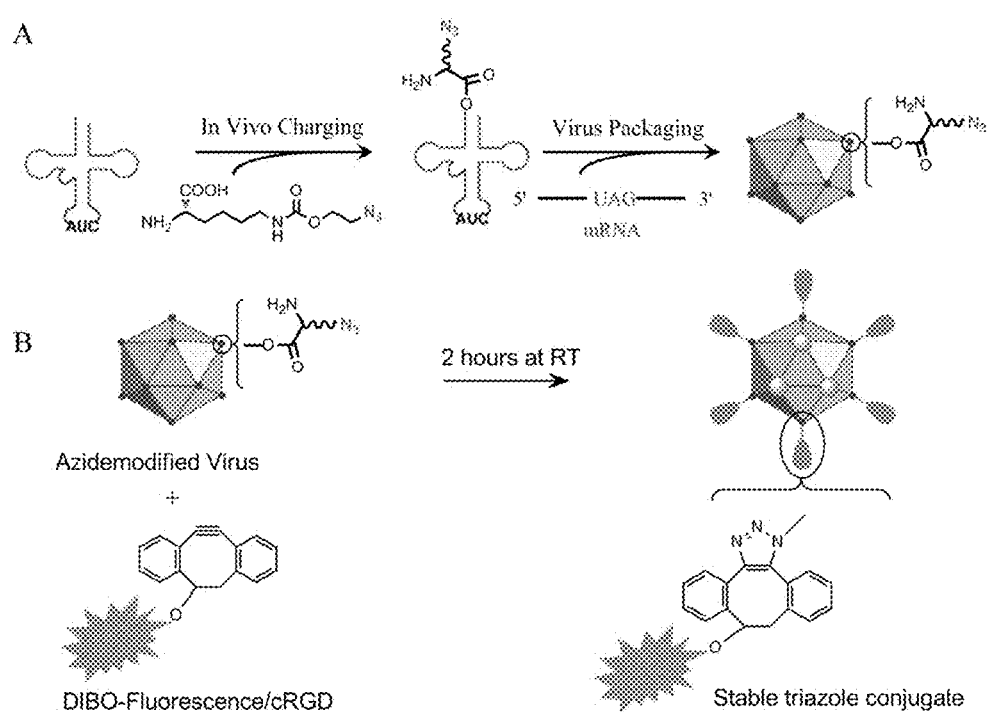
FIG. 1 shows a schematic process for modifying an adeno-associated virus on basis of click chemistry.

In Example 3, we obtained the AAV2 that was site-specifically labeled with NAEK, the azido tag in NAEK label on AAV2 could be used together with DIBO-fluorescence molecule to site-specifically couple a fluorescence group to surface of viral particles via copper-free click chemistry (see FIG. 1).

Copper-free click chemistry is a means of achieving click reactions while maintaining cell viability through the introduction of cyclooctynes, wherein the strain in eight-membered ring allows the reaction with azides to occur in the absence of catalysts. One of such reagents is comprised of the so-called DIBO compounds[18]. Azide-modified macromolecules can now be labeled without a metal catalyst, which not only is useful in studying living cells but also prevents damage of proteins.

To determine whether an azido tag could bioorthogonally react with Alexa 488 under facile and mild conditions (25° C. for 2 hours), the purified wild-type AAV2 (WT-AAV2) and azido-tagged AAV2 particles (R447-AAV2 and S578-AAV2) were produced and reacted with DIBO-Alexa 488 at room temperature for 2 hours, and the reaction buffer was replaced by PBS using 100 kD Millipore Amicon Ultra-100. Subsequently, the viral particle-containing solutions were overlaid onto HeLa cells and immunostained with an antibody specific for intact AAV2 particles. The specific experimental methods could be seen in "fluorescence probe ligation: and "confocal imaging" of the section of Experimental materials and methods.

Most of the hydrazide signals were co-localized with the AAV2 signals (see: FIG. 7A), whereas no significant hydrazide signals were observed for viral particles lacking the azido tag (see: FIG. 7A), indicating that azido groups were efficiently expressed on the surface of AAV2. The label of green fluorescence on AAV2 capsid proteins VP1/VP2/VP3 was further confirmed by SDS-PAGE image, whereas no signal was detected in WT-AAV2 (see: FIG. 7B, FIG. 7C).

Clearly, NAEK was site-specifically displayed on the mutant viruses and fluorophore was indeed coupled to mutant virus via NAEK. Not only R447-AAV2, but also S578-AAV2 was indeed successfully coupled with Alexa 488 (see: FIG. 7A, 7B, 7C).

Furthermore, another fluorophore, Alexa 555, could also be ligated to AAV2 via NAEK (see: FIG. 8) by the same method as above. The above results demonstrated that this azido tag enabled covalent attachment of fluorescent probes to AAV2 particles in a site-specific manner.

It should be noticed that bioorthogonal reaction of viruses with Alexa 488 or 555 had very little, if any, effect on the infectivity of fluorescence-labeled viruses, clearly due to the facile and mild condition (incubated at 25° C. for 2 hours) and also the small size of the probe, NAEK-DIBO-Alexa 488 or 555. It estimates that the probe was approximately 2.6868 nm according to Chem 3D software, just around 1% the size of a single AAV2.

EXAMPLE 5

Observing Single Virus Movement Using Fluorescently-labeled AAV2

Having established the approach for site-specific labeling of AAV2 with Alexa 488, the present invention tested whether such labeling could be used for single virus tracking.

The mutant virus carrying Alexa 488 at site 447 were added to HeLa cells. After incubation at 4° C. for 30 min to synchronize the binding, these viruses were monitored under confocal microscopy by real-time imaging, in which specific experimental methods could be seen in "Confocal imaging" in the section of experimental materials and methods. Various types of intracellular movements of viral particles were observed during imaging, and representative trace of Alexa 488-labeled AAV2 in HeLa cells were shown in FIG. 9 (see: FIG. 9A, 9B, 9C).

Based on the two dimensional data analysis of the three dimensional AAV2 particle movements, we found that many particles exhibited relatively slow movements (e.g., the pink trace in FIG. 9D), while some particles showed fast and directed transport (e.g., orange trace in FIG. 9D)[19]. FIGS. 9D, 9E and 9F showed time trace of viral speeds.

In our analysis, the trace having a peak speed ≥0.002 μm/s and containing unidirectional movement in more than 5 consecutive frames were defined as directed transport, trace with fast (≥0.002 μm/s) but undirectional movement were defined as fast undirected transport, and trace with slow (≤0.002 μm/s) and undirectional movements were defined as slow undirected transport.

Using these definitions, 16.3% of Alexa-AAV2 trace were fast and directed, 24.7% of Alexa-AAV2 trace were fast but undirected, whereas the remaining were slow undirected transport (FIG. 9H).

In order to real-time monitoring the interaction between AAV2 and clathrin, Alexa 488-tagged viruses were co-incubated with Hela cells in which clathrin fused with red fluorescence protein was expressed, and living cell imaging was carried out by using a time-lapse spinning confocal microscopy. The representative trace and pictures of Alexa 488-AAV2 were shown in FIG. 10A. Viral particles (green) firstly were co-localized with clathrin signal (red). This co-localization were continued for about 10 seconds, then the clathrin signal disappeared rapidly, indicating viruses were dissociated from uncoated clathrin vesicles (FIG. 10B). In the first 10 s of co-localization of viral particles and clathrin signals, the instantaneous diffusion coefficients of viral particles were significantly lower than that after dissociation of clathrin signals (FIG. 10C), indicating the viral particles entered cells via the regions defined by clathrin-coated pit.

EXAMPLE 6

Enhancement Effects of Conjugation of AAV2 and Targeting Ligand on Cell Transduction Based on the above experiments, we coupled tumor-targeted motif (cyclic RGD) to AAV2 capsid protein so as to perform targeting delivery of genes. Integrin was was receptor of RGD peptide, and highly expressed in many tumors. Thus, RGD could be used for coating AAV vector to improve delivery efficiency and selectivity of targeted integrin αvβ3 (highly expressed in tumor cells). RAD was a mutant motif of RGD in which glycine was mutated as alanine, and could be used as negative control.

As shown in FIG. 11, the obtained vectors were used to transfect U87 cells (integrin αvβ3 positive cells) and Hela cells (used as negative control). We found that AAV vectors to which RGD coupled at different sites showed different influences on transduction efficiency of U87. At site N587+1, it was observed that transduction efficiency was elevated significantly, by almost 10 times in comparison with the AAV vector that carried RAD and contained azide (control), whereas such elevation was not observed when RGD was coupled to sites 447, 587 and 662. Significant decrease was observed when RGD was coupled to sites 453, 578. As a control, coupling RAD, rather than RGD, to AAV vector had not influence on transduction efficiencies of these sites, indicating RGD played a key role in elevating transduction efficiency. Hence, it was an efficient approach for elevating transduction efficiency of cells that could hardly be transduced to couple RGD to AAV vector at a suitable site, rather than arbitrary sites. As for Hela cells, the conduction efficiency was elevated by only about 20% when RGD was coupled to AAV vector at site 587+1, which might be due to the low expression of integrin αvβ3 on surface of cells (FIG. 11C). The results showed that coupling RGD in such site-selective manner was an efficient approach for regulating tendency of AAV vector and elevating gene delivery efficiency.

In order to further verify that cRGD-labeled AAV2 capsid protein was obtained via "click" reaction between DIBO and NAEK, RAD, RGD, DIBO, RAD-DIBO, RGD-DIBO or a combination thereof was separately incubated with $AAV2^{N587+1\ azido}$. As shown in FIG. 12A, only DIBO-RGD group exhibited an enhanced viral transduction efficiency, and only DIBO molecule could competitively inhibit DIBO-RGD. These results indicated that the RGD peptide as tagged on AAV2 capsid protein was linked via only "click" chemistry between NAEK and DIBO.

In order to verify the above conclusion from another hand, we carried out experiments of using these vectors to competitively inhibit AAV mediated gene delivery. We used a synthesized RGD polypeptide and an anti-integrin antibody to check whether they could inhibit transduction. As shown in FIG. 12B, the GFP expression in U87 cells as mediated by $AAV2^{N587+1\ azido}$+RGD vector could be significantly inhibited by the synthesized RGD polypeptide and anti-integrin antibody. These results showed that the interaction between cell surface RGD and integrin was specific.

Subsequently, we wanted to know whether cRGD-chemically modified AAV2 had better effects than RGD fused on AAV2 surface. As shown in FIG. 13, when the cRGD-chemically modified AAV2 and the RGD fused on AAV2 surface were compared with unmodified AAV2 (wild-type AAV2), they both could significantly improve viral transduction efficiency. However, the viral transduction efficiency of the cRGD-chemically modified AAV2 was 1.5 times of that of the RGD fused on AAV2 surface. These results indicated that the method for site-specifically modifying AAV2 in the present invention was superior to the method for virus-targeting AAV2 surface modification.

In order to reveal why the cRGD chemical modification of AAV2 was superior to the RGD surface fusion of AAV2, we analyzed binding ability of virus to cells. Different kinds of virus with same amount were incubated with U87 cells at 4° C. for 2 h, then analysis was carried out by using anti-AAV monoclonal A20 and FACS. As shown in FIG. 14, in comparison with the unmodified AAV2 or linear RAD modified AAV2, both of the cRGD chemically modified AAV2 and the RGD fusion modified AAV2 showed significant improvement of virus binding ability. However, the binding ability of the cRGD chemically modified AAV2 was still 1.5 times of that of the RGD fusion modified AAV2. The results showed that the cRGD chemically coupled AAV2 had cell binding ability significantly superior to that of the RGD fusion modified AAV2, and thus had better virus targeting effect.

In the above works, we packaged GFP reporter gene in viral capsid to facilitate researches. If GFP gene was replaced with a therapeutic gene, did virus still exhibit the above features? In the experiments, we packaged herpes simplex virus thymidine kinase (HSV-tk) gene and tumor necrosis factor-associated apoptosis ligand (TRAIL) gene, which had cell killing function, into NAEK labeled virus, and cRGD molecule was coupled via NAEK, so as to prepare RGD chemically free modified virus $AAV^{N587+1/azido}$+RGD-TK/TRAIL. The experimental results showed that $AAV^{N587+1/azido}$+RGD-TK/TRAIL virus had a tumor cell killing effect superior to those of WT-AAV and RGD fusion modified $AAV^{N587+RGD}$-TK/TRAIL virus. However, their killing effects on Hela cells with low expression of integrin showed no significant difference. This indicated that the cRGD chemical free modification not only enhanced the killing effects of virus, but also improved the targeting capacity of virus (FIG. 15, 16).

EXAMPLE 7

Preparation of Photocrosslinking Non-natural Amino Acid (DiZPK) Site-specifically Labeled AAV2

By using the method same as above, photocrosslinking non-natural amino acid (DiZPK) was site-specifically introduced to AAV2 capsid surface, which could capture new interacted proteins via photocrosslinking during the process that virus entered cells, thereby finding new receptors of virus. As shown in FIG. 17, trials had been carried out at sites S261, R447, F534, T573, N587, and it was so far found that DiZPK could be successfully introduced at site N587.

In view of research results, at site R447, NAEK could be introduced, but DiZPK could not be incorporated, while at site N587, both of these two non-natural amino acids could be incorporated. The reason for this could be that each amino acid residue site of protein molecule had different spatial structure, and required different structure of non-natural amino acid to be introduced.

Although the present invention have been described in details in the specific models for carrying out the invention, those skilled in the art would understand that these details could be modified and replaced according all disclosed teachings, and all of these changes fall within the protection scope of the present invention. The whole scope of the present invention is given by the affixed claims and any equivalents thereof.

REFERENCES

1. Atchison R W, Casto B C, Hammon W M: Adenovirus-Associated Defective Virus Particles. *Science* 1965, 149 (3685):754-756.
2. Gray S J, Samulski R J: Optimizing gene delivery vectors for the treatment of heart disease. *Expert Opin Biol Ther* 2008, 8(7):911-922.
3. Grimm D, Kay M A: From virus evolution to vector revolution: use of naturally occurring serotypes of adeno-associated virus (AAV) as novel vectors for human gene therapy. *Curr Gene Ther* 2003, 3(4):281-304.
4. Mueller C, Flotte T R: Clinical gene therapy using recombinant adeno-associated virus vectors. *Gene Ther* 2008, 15(11):858-863.
5. Choi K J, Kim J H, Lee Y S, Kim J, Suh B S, Kim H, Cho S, Sohn J H, Kim G E, Yun C O: Concurrent delivery of GM-CSF and B7-1 using an oncolytic adenovirus elicits potent antitumor effect. *Gene Ther* 2006, 13(13): 1010-1020.
6. Wu Z, Asokan A, Samulski R J: Adeno-associated virus serotypes: vector toolkit for human gene therapy. *Mol Ther* 2006, 14(3):316-327.
7. Fisher K J, Jooss K, Alston J, Yang Y, Haecker S E, High K, Pathak R, Raper S E, Wilson J M: Recombinant adeno-associated virus for muscle directed gene therapy. *Nat Med* 1997, 3(3):306-312.
8. Moss R B, Rodman D, Spencer L T, Aitken M L, Zeitlin P L, Waltz D, Milla C, Brody A S, Clancy J P, Ramsey B et al: Repeated adeno-associated virus serotype 2 aerosol-mediated cystic fibrosis transmembrane regulator gene transfer to the lungs of patients with cystic fibrosis: a multicenter, double-blind, placebo-controlled trial. *Chest* 2004, 125(2):509-521.
9. Mingozzi F, High K A: Therapeutic in vivo gene transfer for genetic disease using AAV: progress and challenges. *Nat Rev Genet,* 12(5):341-355.
10. Bainbridge J W, Smith A J, Barker S S, Robbie S, Henderson R, Balaggan K, Viswanathan A, Holder G E, Stockman A, Tyler N et al: Effect of gene therapy on visual function in Leber's congenital amaurosis. *N Engl J Med* 2008, 358(21):2231-2239.
11. Hauswirth W W, Aleman T S, Kaushal S, Cideciyan A V, Schwartz S B, Wang L, Conlon T J, Boye S L, Flotte T R, Byrne B J et al: Treatment of leber congenital amaurosis due to RPE65 mutations by ocular subretinal injection of adeno-associated virus gene vector: short-term results of a phase I trial. *Hum Gene Ther* 2008, 19(10):979-990.
12. Manno C S, Pierce G F, Arruda V R, Glader B, Ragni M, Rasko J J, Ozelo M C, Hoots K, Blatt P, Konkle B et al: Successful transduction of liver in hemophilia by AAV-Factor IX and limitations imposed by the host immune response. *Nat Med* 2006, 12(3):342-347.
13. Manno C S, Chew A J, Hutchison S, Larson P J, Herzog R W, Arruda V R, Tai S J, Ragni M V, Thompson A, Ozelo M et al: AAV-mediated factor IX gene transfer to skeletal muscle in patients with severe hemophilia B. *Blood* 2003, 101(8):2963-2972.
14. White S J, Nicklin S A, Buning H, Brosnan M J, Leike K, Papadakis E D, Hallek M, Baker A H: Targeted gene 15. Yu C Y, Yuan Z, Cao Z, Wang B, Qiao C, Li J, Xiao X: A muscle-targeting peptide displayed on AAV2 improves muscle tropism on systemic delivery. *Gene Ther* 2009, 16(8):953-962.

16. Work L M, Buning H, Hunt E, Nicklin S A, Denby L, Britton N, Leike K, Odenthal M, Drebber U, Hallek M et al: Vascular bed-targeted in vivo gene delivery using tropism-modified adeno-associated viruses. *Mol Ther* 2006, 13(4): 683-693.

17. Douar A M, Poulard K, Danos O: Deleterious effect of peptide insertions in a permissive site of the AAV2 capsid. *Virology* 2003, 309(2):203-208.

18. Ning X, Guo J, Wolfert M A, Boons G J: Visualizing metabolically labeled glycoconjugates of living cells by copper-free and fast huisgen cycloadditions. *Angew Chem Int Ed Engl* 2008, 47(12):2253-2255.

19. Joo K I, Fang Y, Liu Y, Xiao L, Gu Z, Tai A, Lee C L, Tang Y, Wang P: Enhanced real-time monitoring of adeno-associated virus trafficking by virus-quantum dot conjugates. *ACS Nano,* 5(5):3523-3535.

20. Rohr, U. P.; Wulf, M. A.; Stahn, S.; Steidl, U.; Haas, R.; Kronenwett, R. *J Virol Methods* 2002, 106, 81-8.

21. Travis S. Young and Peter G. Schultz: Beyond the Canonical 20 Amino Acids: Expanding the Genetic Lexicon. *J. Biol. Chem.* 2010, 285:11039-11044.

22. Jianming Xie and Peter G Schultz: Adding amino acids to the genetic repertoire. Current Opinion in Chemical Biology 2005, 9:548-554.

---

What is claimed is:

1. A site-specifically mutated adeno-associated virus capsid protein VP1 or a fragment thereof, wherein an amino acid at a specific site of a corresponding wild type adeno-associated virus capsid protein VP1 or a fragment thereof is mutated as an non-natural amino acid, and the specific site is at least one site selected from sites R447, G453, S578, N587, N587+1, S662 of VP1 or fragment thereof, wherein the non-natural amino acid is Nε-2-azideoethyl-oxycarbonyl-L-lysine (NAEK),

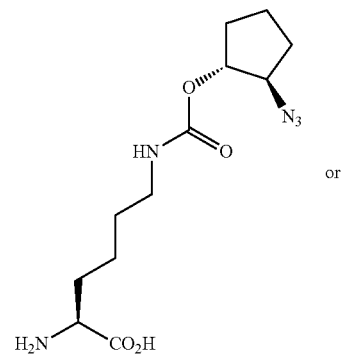

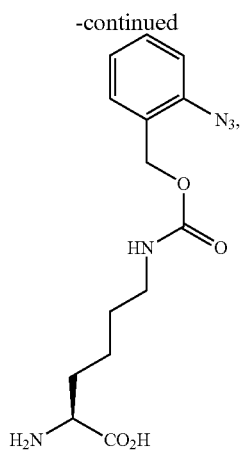

or the non-natural amino acid is an non-natural amino acid with structure DiZPK.

2. A site-specifically mutated adeno-associated virus capsid protein VP1 or a fragment thereof, wherein an amino acid at a specific site of a corresponding wild type adeno-associated virus capsid protein VP1 or a fragment thereof is mutated as an non-natural amino acid, and the specific site is at least one site selected from sites R447, G453, S578, N587, N587+1, S662 of VP1 or fragment thereof;

wherein the non-natural amino acid is an azido-containing non-natural amino acid, Nε-2-azideoethyloxycarbonyl-L-lysine (NAEK),

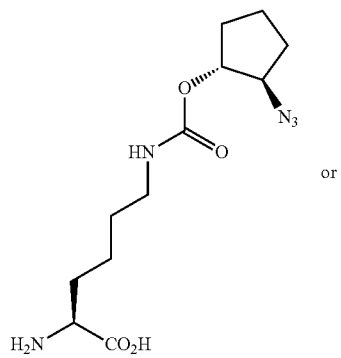

or

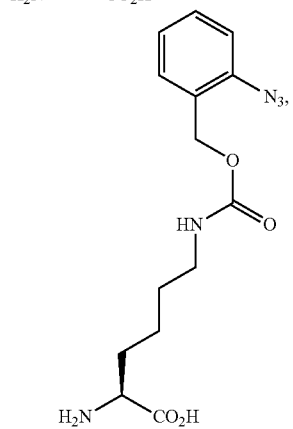

or the non-natural amino acid is an non-natural amino acid with structure DiZPK;

wherein the NAEK and the amino acid sequence of VP1 or fragment thereof are linked as shown in Formula I:

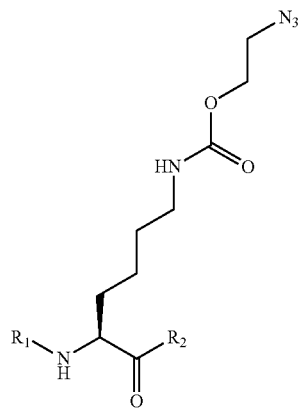

wherein the direction from R1 to R2 is the direction from N-terminal to C-terminal of the amino acid sequence, in which amino acid at site N is one of amino acids at sites selected from site R447, site G453, site S578, site N587, site N587+1, site S662, R1 is an amino acid residue at site 1 to site N-1 of the amino acid sequence of VP1 or fragment thereof, R2 is an amino acid residue at site N+1 to C-terminal of the amino acid sequence of VP1 or fragment thereof;

wherein the DiZPK and the amino acid sequence of VP1 or fragment thereof are linked as shown in Formula II:

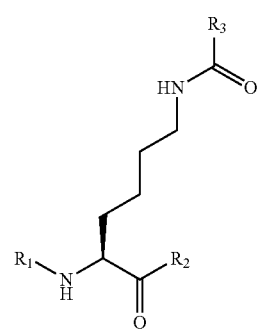

wherein the direction from R1 to R2 is the direction from N-terminal to C-terminal of the amino acid sequence, in which amino acid at site N is one of amino acids at sites selected from site R447, site G453, site S578, site N587, site N587+1, site S662, R1 is an amino acid residue at site 1 to site N-1 of the amino acid sequence of VP1 protein or fragment thereof, R2 is an amino acid residue at site N+1 to C-terminal of the amino acid sequence of VP1 protein or fragment thereof, R3 is

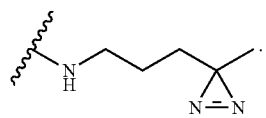 [SMILES: *NCCCC1(C)N=N1]

3. The site-specifically mutated adeno-associated virus capsid protein VP1 or a fragment thereof according to claim 2, wherein the adeno-associated virus is type II adeno-associated virus.

4. The site-specifically mutated adeno-associated virus capsid protein VP1 or a fragment thereof according to claim 2, wherein the non-natural amino acid further links to a labeling group, fluorescence labeling group, or a labeling group capable of occurring a click chemistry with azide; or the non-natural amino acid further links to a targeting molecule, preferably, the targeting molecule further links to a group capable of occurring a click chemistry with azide.

5. A site-specifically mutated adeno-associated virus capsid protein, comprising the adeno-associated virus capsid protein VP1 or fragment thereof according to claim 2.

6. A site-specifically mutated adeno-associated virus, comprising the adeno-associated virus capsid protein VP1 or fragment thereof according to claim 2.

7. The adeno-associated virus according to claim 6, wherein the non-natural amino acid further links to a labeling group, a fluorescence labeling group, or a labeling group capable of occurring a click chemistry with azide.

8. The adeno-associated virus according to claim 6, wherein the non-natural amino acid further links to a targeting molecule, preferably, the targeting molecule further links to a group capable of occurring a click chemistry with azide.

9. The adeno-associated virus according to claim 6, which carries a functional nucleic acid fragment or a nucleic acid fragment of a labeling molecule.

10. A composition or kit, which comprises the adeno-associated virus according to claim 2.

11. A gene vaccine, which comprises the adeno-associated virus according to claim 2.

12. A composition or kit, which comprises the adeno-associated virus according to claim 6.

13. A gene vaccine, which comprises the adeno-associated virus according to claim 6.

14. The site-specifically mutated adeno-associated virus capsid protein VP1 or a fragment thereof according to claim 1, wherein the adeno-associated virus is type II adeno-associated virus.

15. The site-specifically mutated adeno-associated virus capsid protein VP1 or a fragment thereof according to claim 1, wherein the non-natural amino acid further links to a labeling group, fluorescence labeling group, or a labeling group capable of occurring a click chemistry with azide; or the non-natural amino acid further links to a targeting molecule, preferably, the targeting molecule further links to a group capable of occurring a click chemistry with azide.

16. A site-specifically mutated adeno-associated virus capsid protein, comprising the adeno-associated virus capsid protein VP1 or fragment thereof according to claim 1.

17. A site-specifically mutated adeno-associated virus, comprising the adeno-associated virus capsid protein VP1 or fragment thereof according to claim 1.

18. The adeno-associated virus according to claim 17, wherein the non-natural amino acid further links to a labeling group, a fluorescence labeling group, or a labeling group capable of occurring a click chemistry with azide.

19. The adeno-associated virus according to claim 17, wherein the non-natural amino acid further links to a targeting molecule, preferably, the targeting molecule further links to a group capable of occurring a click chemistry with azide.

20. The adeno-associated virus according to claim 17, which carries a functional nucleic acid fragment or a nucleic acid fragment of a labeling molecule.

21. A composition or kit, which comprises the adeno-associated virus according to claim 1.

22. A gene vaccine, which comprises the adeno-associated virus according to claim 1.

23. A composition or kit, which comprises the adeno-associated virus according to claim 17.

24. A gene vaccine, which comprises the adeno-associated virus according to claim 17.

* * * * *